(12) United States Patent
Stone

(10) Patent No.: US 6,353,149 B1
(45) Date of Patent: Mar. 5, 2002

(54) FAST BLOOMING SURFACTANTS FOR USE IN FLUID TRANSPORT WEBS

(75) Inventor: Keith Joseph Stone, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/287,986

(22) Filed: Apr. 8, 1999

(51) Int. Cl.[7] .................................................. A61F 13/15
(52) U.S. Cl. ........................ 604/372; 604/367; 604/375; 604/378; 428/98; 428/131
(58) Field of Search .................................. 510/295, 296, 510/297, 520; 604/540, 372, 367, 378, 358, 375, 369, 384; 427/244; 252/8, 8.6, 398, 113, 220; 428/196, 262, 400, 297, 401, 289, 376, 537, 397, 131, 119, 167, 83; 442/189, 195, 196, 192, 334, 335, 337; 521/64, 62, 63, 146; 206/5; 8/137, 358

(56) References Cited

U.S. PATENT DOCUMENTS

| 4,070,218 A | | 1/1978 | Weber | |
|---|---|---|---|---|
| 4,095,946 A | * | 6/1978 | Jones et al. ..................... | 8/137 |
| 4,113,630 A | * | 9/1978 | Hagner et al. ................ | 252/8.6 |
| 4,118,525 A | * | 10/1978 | Jones .......................... | 427/242 |
| 4,121,009 A | * | 10/1978 | Chakrabarti ................ | 428/260 |
| 4,220,562 A | * | 9/1980 | Spadini et al. .............. | 252/542 |
| 4,342,314 A | | 8/1982 | Radel et al. | |
| 4,463,045 A | | 7/1984 | Ahr et al. | |
| 4,535,020 A | | 8/1985 | Thomas et al. | |
| 4,578,414 A | | 3/1986 | Sawyer et al. | |
| 4,629,643 A | | 12/1986 | Curro et al. | |
| 4,735,843 A | | 4/1988 | Noda .......................... | 428/137 |
| 4,898,680 A | * | 2/1990 | Clauss et al. ................ | 252/8.8 |
| 4,923,914 A | | 5/1990 | Nohr et al. | |
| 5,112,690 A | | 5/1992 | Cohen et al. ............. | 428/411.1 |
| 5,439,734 A | | 8/1995 | Everhart et al. | |
| 5,520,875 A | | 5/1996 | Wnuk et al. | |
| H1670 H | | 7/1997 | Aziz et al. | |
| 5,643,588 A | | 7/1997 | Roe et al. ..................... | 424/402 |
| 5,763,499 A | * | 6/1998 | DesMarais ................... | 521/64 |
| 5,792,412 A | | 8/1998 | Lee et al. | |
| 5,899,893 A | * | 5/1999 | Dyer et al. .................. | 604/358 |
| 5,951,535 A | * | 9/1999 | Fujiwara et al. ............ | 604/384 |
| 5,972,505 A | * | 10/1999 | Phillips et al. .............. | 428/397 |

FOREIGN PATENT DOCUMENTS

| EP | 683260 A2 | 11/1995 |
|---|---|---|
| WO | WO 96/00548 | 1/1996 |

* cited by examiner

Primary Examiner—John G. Weiss
Assistant Examiner—Michaerl Bogart
(74) Attorney, Agent, or Firm—Edward J. Milbrada; Caroline Wei-Berk; Ken K. Patel

(57) ABSTRACT

Disclosed are fast blooming surfactants that are suitable for inclusion in film compositions that will subsequently treated with a low surface energy material to create a surface energy gradient between the underlying polymeric structure of the film and spaced apart microscopic depositions of the low surface energy material. The surfactants have a permeation rate of less than 240 hours, a surface tension in an aqueous solution at a concentration that is greater than the critical micelle concentration that lies between the critical surface tension of the underlying polymeric structure of the web material and the critical surface tension of the low surface energy depositions; and an HLB between about 6 and about 16. Preferred surfactants also have a weight loss on heating to 250° C. that is less than about 20%. More preferred surfactants have a hydrophobic chain that is substantially saturated.

20 Claims, 7 Drawing Sheets

FAST BLOOMING SURFACTANTS FOR USE IN FLUID TRANSPORT WEBS

FIELD OF THE INVENTION

The present invention relates to a web which is suitable for use as a fluid transport mechanism. In particular, the present invention relates to fast blooming surfactants that co-operate with other components of the web to enable a surface energy gradient which facilitates fluid transport in a preferential direction from one surface toward another surface and resist fluid transport in the opposite direction.

BACKGROUND OF THE INVENTION

It has long been known in the field of disposable absorbent articles that it is extremely desirable to construct absorptive devices, such as disposable diapers, sanitary napkins, incontinent briefs, bandages, wound dressings, and the like, presenting a dry surface feel to the user to improve wearing comfort and to minimize the potential for development of undesirable skin conditions due to the prolonged exposure to moisture absorbed within the article. Accordingly, it is generally desirable to promote rapid fluid transfer in a direction away from the wearer and into a retentive structure, while resisting fluid transfer in the reverse direction.

One viable prior art solution to the aforementioned problem has been to utilize a covering or topsheet on the exposed, wearer-contacting surface which comprises a web of formed, apertured thermoplastic film. Commonly assigned U.S. Pat. No. 4,342,314, issued to Radel et al. on Aug. 3, 1982, the disclosure of which is hereby incorporated herein by reference, discloses a representative formed film of this variety. Such webs utilize capillary fluid transport to conduct fluid away from one surface (wearer-contacting) into and through the web via three-dimensional capillaries formed into the material, and then into the underlying absorbent structure. In order to address consumer concerns with regard to plastic-like appearance and feel, webs of this variety have been developed which include an interconnected structure of fiber-like appearance in the interest of generating a more clothlike, aesthetically-pleasing appearance. In addition, apertured, formed thermoplastic film webs have been developed which further include microscopic surface texturing (microtexture) and/or microscopic apertures (microapertures) to further enhance the visual and tactile impression of such webs. Representative film webs of this variety are discloses in commonly assigned U.S. Pat. No. 4,463,045, issued to Ahr et al. on Jul. 31, 1984, and U.S. Pat. No. 4,629,643, issued Dec. 16, 1986 to Curro et al., the disclosures of which are hereby incorporated herein by reference.

Another viable prior art solution has been to utilize a fibrous material as a covering or topsheet on such articles, alone or as an overlay or laminate over other materials. A representative topsheet structure of this variety is disclosed in Statutory Invention Registration H1670 published in the name of Aziz et al. on Jul. 1, 1997, the disclosure of which is hereby incorporated herein by reference. Such fibrous materials may take the form of a woven or nonwoven web of a suitable fiber variety, and may or may not include discretely formed apertures in addition to the inherent porosity of the web itself. Webs of this variety also exhibit capillary fluid transport characteristics via the three-dimensional capillaries formed by inter-fiber spaces, likewise conducting fluid away from the wearer-contacting surface and into the underlying absorbent structure. Such webs exhibit an aesthetically-pleasing, cloth-like surface appearance and tactile impression due to the fibrous nature of the surface.

While capillary webs of the foregoing varieties are effective in transporting fluid, their effectiveness is limited in that such capillary structures can only move fluid once it reaches the capillary interior. Fluid which wets and remains on wearer contacting surfaces contributes to a "wet" tactile feeling or impression, and to the extent that such fluid may be colored or opaque also contributes to a "stained" visual impression. Surface textures naturally occurring in the material of the web or imparted thereto in formation further increase the likelihood that residual fluid will be trapped or retained on the wearer-contacting surface rather than entering capillary structures for transport away from the surface. Thus, surface topographies which contribute to desirable visual and tactile impressions when dry can also tend to retain residual fluid on the exposed surface and thus reduced desirability under in-use conditions.

Such wetting is further exacerbated by the use of surfactant materials to encourage flow of bodily fluids on the surface of such webs. The use of surfactant materials is described, for example, in U.S. Pat. 4,535,020, issued in the name of Thomas, et al. on Aug. 13, 1985 which describe incorporating a surfactant material into the polymer blend used to produce a perforated film material. The perforated films described therein are said to have much higher liquid transmission rates than similarly made non surfactant treated perforated films. Similarly, U.S. Pat. No. 5,520,875, issued in the name of Wnuk, et al on May 28, 1996, describes incorporating a surfactant into a coextruded multilayer polymeric film that is formed into an apertured web.

The art has also discussed various surfactants as being useful for incorporation into polymeric matrices. For example U.S. Pat. No. 4,070,218, issued to Weber on Jan. 24, 1978, discloses incorporating nonionic surfactant materials into the polymer that is extruded to form a nonwoven web. The materials are said to be useful as lubricating agents for softening the web. The reference further teaches heating the web to cause the material to migrate to the surface. While such materials may be suitable for softening the web, webs using such materials would have a hydrophilic surface and would still suffer the same deficiencies with fluid retention that are discussed above. Further, the reference teaches the necessity of an added heating process step to cause the materials to come to the surface.

U.S. Pat. No. 5,439,734, issued to Everhart and Meirowitz on Aug. 8 1995, also teaches the necessity of post extrusion heat activation. Further, the surfactant material that is described most completely has an unsaturated hydrophobe. As is known, such unsaturated materials may be oxidatively unstable, producing degradation products having unpleasant odors.

U.S. Pat. No. 4,578,414, issued in the names of Sawyer and Knight on Mar. 25, 1986, teaches surfactants having a high degree of ethoxylation. As is known, a high degree of ethoxylation will require a high molecular weight hydrophobe in order to maintain a mid-range HLB (desirable for wetting performance). Such molecular weight increases can lead to undesirable slow blooming.

U.S. Pat. No. 4,923,914, issued to Nohr and McDonald on May 8, 1990 and European Patent Application EP 683,260 A2, published in the names of Yahiaoul, Perkins, and Jascomb on Nov. 22, 1995 both teach the desirability of using surfactant materials that are very efficient wetting agents. In particular, the references teach the desirability of siloxane-based and/or fluorocarbon-based hydrophobes. While such surfactant materials may be very efficient in providing a wettable surface, if the surfactant is too efficient, it will eliminate the aforementioned surface energy gradient that has been found to be desirable for fluid transport purposes.

The art has addressed the problem of transporting fluids away from a wearer contacting surface while retaining desirable visual and tactile properties by providing pervious webs (e.g. via fluid passageways provided by apertures or interfiber capillaries) treated so as to have microscopic, discontinuous, spaced apart depositions of a low surface energy material on at least the wearer contacting surface. The low surface energy material provides a surface energy gradient between the material and the remainder of the body surface that exerts a force on any fluid contacting the body surface to direct such fluid toward and into the fluid passageways for transportation away from the body surface and into an absorbent article when such webs are used as a topsheet in an absorbent article. Webs treated so as to have such a surface energy gradient are described in U.S. Pat. No. 6,025,049 issued in the name of Ouellette, et al. on Feb. 15, 2000. While webs having a surface energy gradient have desirable fluid transport properties, surfactants known to the prior art as being preferable for increasing liquid transmission rates through untreated webs, have undesirably low permeabilities through such treated webs. In particular, it has been found that, those components of such prior art surfactants that permeate through such treated webs rapidly have insufficient surfactant activity to provide a desirable balance of acquisition and rewet reduction. Conversely, those components having sufficient surfactant activity so as to be effective permeate much more slowly. Such low permeability of preferable surfactant components results in an undesirably long delay before webs using prior art surfactant materials and low surface energy depositions have the desirable balance of fluid acquisition and rewet reduction.

Accordingly, it would be desirable to provide a web having an effective balance of enhanced effectiveness in transporting fluid away from the surface which is initially contacted by a fluid and prevention of rewetting of that surface by absorbed fluid, wherein the web is available for conversion into a finished product without a long induction period before the web has suitable fluid handling properties. More particularly, it would be desirable to provide the underlying polymeric structure that forms the base of such webs with surfactant materials with surfactant materials incorporated therein having a high permeation rate through webs treated with low surface energy materials which results in fast blooming of active surfactant components to the surface of the web so such webs are quickly available for conversion into finished absorbent articles. It would be also desirable if such surfactant materials have satisfactorily high thermal stability and/or low volatility so the surfactant material does not undesirably build up on equipment components when such surfactant materials as are incorporated into the polymer composition used to extrude the underlying polymeric structure that forms the base for webs having the above-mentioned desirable balance of acquisition and rewet reduction. Finally, it is desirable that such surfactant materials, when incorporated into a web that will ultimately be converted as a component of an absorbent article, retain the fluid handling properties after long storage periods.

SUMMARY OF THE INVENTION

The present invention comprises fluid permeable webs having a fast blooming surfactants incorporated therein and treated with a low surface energy material to create a surface energy gradient between the underlying polymeric structure of the web and spaced apart microscopic depositions of the low surface energy material. The surfactants have a permeation rate of less than 240 hours and a surface tension in an aqueous solution at a concentration that is greater than the critical micelle concentration that lies between the critical surface tension of the underlying polymeric structure of the web material and the critical surface tension of the low surface energy depositions. Preferred surfactants also have a weight loss on heating to 250° C. that is less than about 20%. More preferred surfactants have a hydrophobic chain that is substantially saturated.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

in FIG. 7a the droplet is located over and extends partially into the generic capillary; in FIG. 7b the droplet is located inside the generic capillary;

DETAILED DESCRIPTION OF THE PRESENT INVENTION

Figure 1:
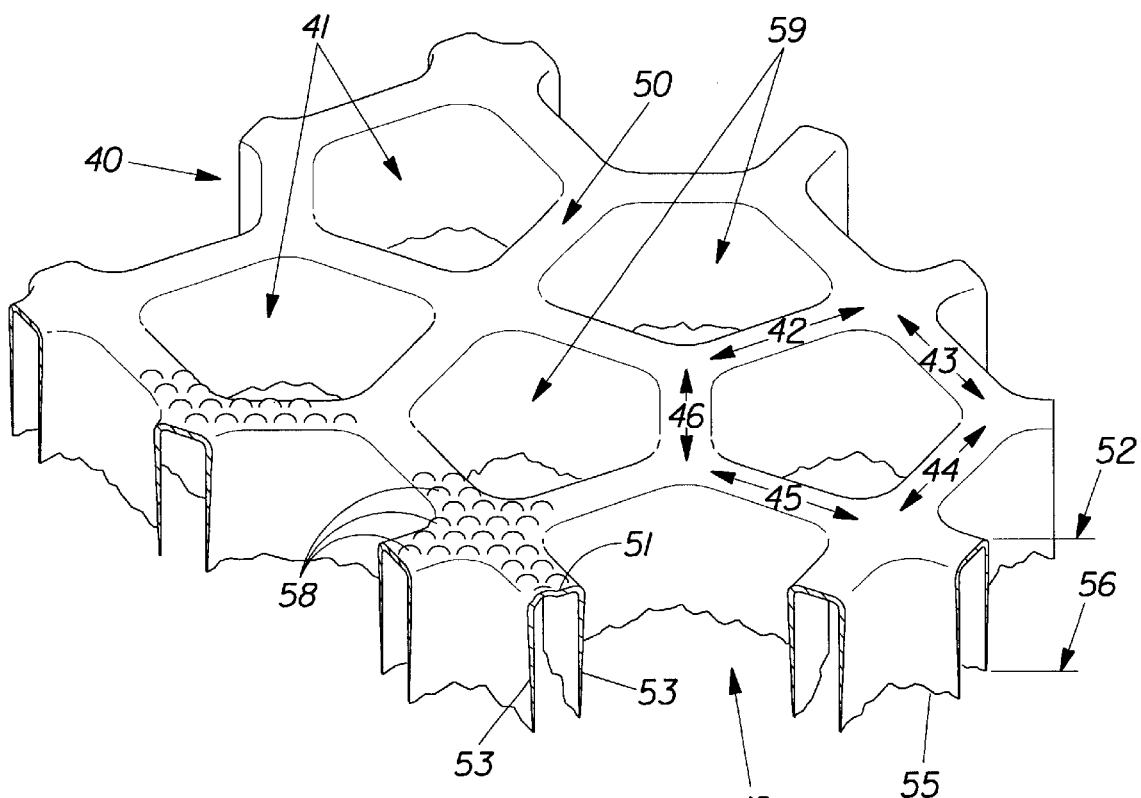
FIG. 1 is an enlarged, partially segmented, perspective illustration of a prior art plastic web of the type generally disclosed in U.S. Pat. No. 4,342,314.
Figure 11:
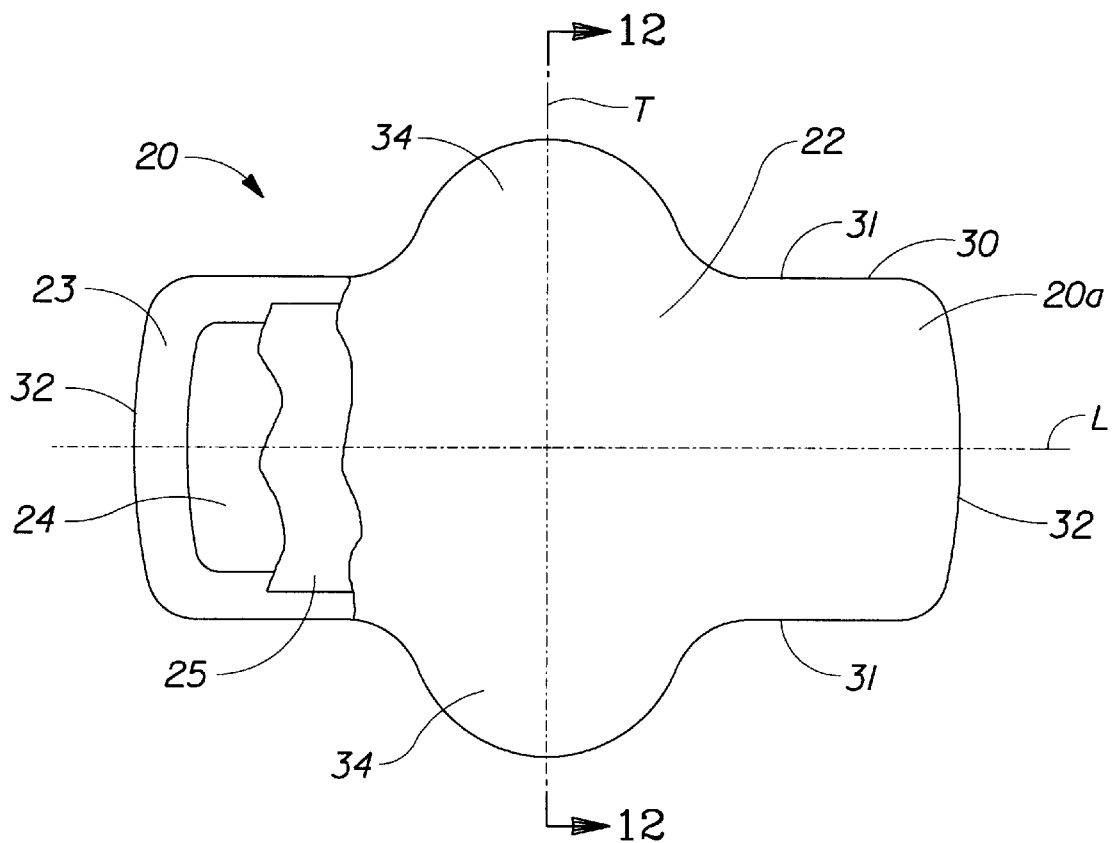
FIG. 11 is a top plan view of a sanitary napkin with portions of the sanitary napkin cut away to more clearly show the construction of the sanitary napkin.
Figure 12:
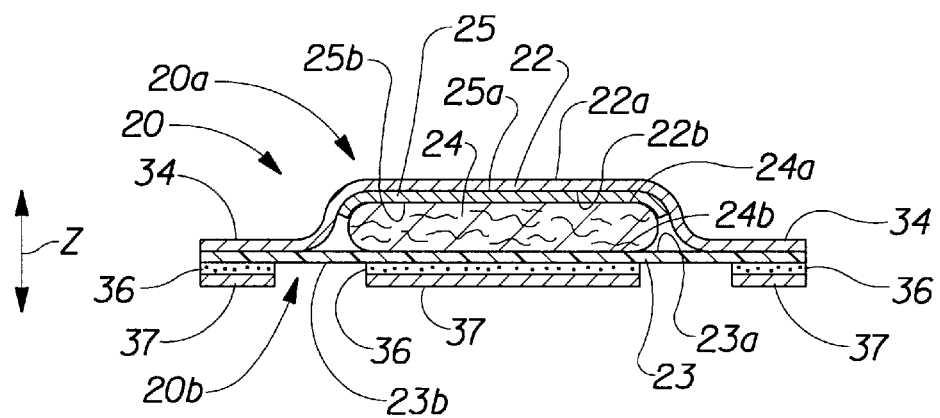
FIG. 12 is a cross-sectional view of the sanitary napkin of FIG. 11 taken along section line 12—12.

FIG. 1 is an enlarged partially segmented, perspective illustration of a prior art resilient, three-dimensional, fluid pervious plastic web 40 exhibiting a combination of fiber-like and plastic properties which has been found highly suitable for use as a topsheet in disposable absorbent articles, such as a sanitary napkin topsheet 22 in a sanitary napkin 20 of the type generally illustrated in FIGS. 11 and 12. The prior art web 40 is generally in accordance with the teachings of commonly assigned U.S. Pat. No. 4,342,314 issued to Radel et al. on Aug. 3, 1982, the disclosure of which is hereby incorporated herein by reference. The fluid pervious plastic web 40 exhibits a multiplicity of apertures (e.g., apertures 41) which are formed by a multiplicity of intersecting fiber-like elements (e.g., elements 42, 43, 44, 45, and 46) interconnected to one another in the first or wearer-contacting surface 50 of the web. Each fiber-like element comprises a base portion (e.g., base portion 51) located in plane 52, and each base portion has a sidewall portion (e.g., sidewall portions 53) attached to each edge thereof The sidewall portions preferably extend generally in the direction of the second surface 55 of the web, with the intersecting sidewall portions of the fiber-like elements interconnected to one another intermediate the first and second surfaces of the web, terminating substantially concurrently with one another in the plane 56 of the second surface 55.

The term "fiber-like", as utilized herein to describe the appearance of plastic webs, refers generally to any fine scale pattern of embossments or apertures, random or non-random, reticulated or non-reticulated, which can provide an overall appearance and impression of a woven or nonwoven fibrous web when viewed by the human eye. When describing the elements used to form the web, the term "fiber-like" is utilized herein to describe the appearance or shape of the elements. As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to a normal human eye when the perpendicular distance between the viewer's eye and the plane of the web is about 12 inches.

In general, as utilized herein the term "macroscopic" is used to refer to structural features or elements which are readily visible to a normal human eye when the perpendicular distance between the viewer's eye and the plane of the web is about 12 inches. Conversely, the term "microscopic" is utilized to refer to structural features or elements which are not readily visible to a normal human eye when the perpendicular distance between the viewer's eye and the plane of the web is about 12 inches.

Such macroscopically expanded webs, ribbons and films are typically caused to conform to the surface of said forming structures by embossing (i.e., when the forming structure exhibits a pattern comprised primarily of male projections), by debossing (i.e., when the forming structure exhibits a pattern comprised primarily of female capillary networks), or by extrusion of a resinous melt onto the surface of a forming structure of either type. By way of contrast, the term "planar" when utilized herein to describe plastic webs, ribbons and films, refers to the overall general condition of the web, ribbon and film when viewed by the naked eye on a macroscopic scale.

In a particularly preferred embodiment, the interconnected sidewall portions 53 terminate substantially concurrently with one another in the plane 56 of the second surface 55 to form apertures 49 in the second surface 55 of the web. The capillary networks 59 formed by the interconnected sidewall portions allows for the free transfer of fluid from the first or wearer-contacting surface 50 of the web directly to the second surface 55 of the web without lateral transmission of fluid between adjacent capillary networks.

Each of the fiber-like elements exhibits a substantially uniform U-shaped cross-section along its length. In the case of a primary fiber-like element, its cross-section comprises a base portion located in the wearer-contacting plane and a sidewall portion joined to each edge of the base portion and extending generally in the direction of the absorbent pad-contacting surface of the web. The sidewall portions which intersect one another are joined to one another intermediate the wearer-contacting surface and the absorbent pad-contacting surface of the web, thereby forming a capillary network interconnecting the opposed surfaces of the web.

One drawback associated with the use of topsheets comprised of plastic is that despite their superior fluid handling characteristics some users are very reluctant to place a topsheet which they readily perceive as plastic by virtue of its glossy appearance in contact with their skin. To reduce the gloss on the web's visible surface, i.e., that portion of the web which is visible from directly overhead, it has been learned that the inclusion of a microscopic pattern of surface aberrations which are not discernible when the perpendicular distance between the viewer's eye and the plane of the web is about 12 inches is highly effective. Commonly assigned U.S. Pat. No. 4,463,045, issued to Ahr et al. on Jul. 31, 1984, the disclosure of which is hereby incorporated herein by reference, defines the relevant criteria which must be satisfied so that the three-dimensionally expanded web will exhibit a substantially non-glossy visible surface.

In a particularly preferred embodiment, the base portion 51, includes a microscopic pattern of surface aberrations 58, generally in accordance with the teachings of the aforementioned '045 Ahr et al. patent. The microscopic pattern of surface aberrations 58 provides a substantially non-glossy visible surface when the web is struck by incident light rays.

A topsheet of the type generally disclosed in Radel et al., having surface aberrations according to Ahr et al., exhibits a fiber-like appearance and tactile impression as well as a non-glossy visible surface. In addition, it is highly effective in promoting rapid fluid transfer from the first or wearer-contacting surface to the second or absorbent pad-contacting surface of the topsheet and in impeding rewet by absorbed bodily fluids because such materials resist compression pressures typical of those created by in-use conditions. Topsheets of the latter type have enjoyed widespread commercial success on catamenial pads due to their clean and dry appearance in use when contrasted to conventional nonwoven fibrous topsheets.

Typically, a prior art web 40 used as a topsheet on an absorbent article is treated with a surfactant to render the topsheet hydrophilic. As noted above, the exposed surfaces of the base portions 51 and the sidewall portions 53 are generally provided with a surfactant such that they will both be rendered substantially hydrophilic, thereby diminishing the likelihood that body fluids will flow off the topsheet rather than being drawn through the topsheet and thereby absorbed by the absorbent core. Suitable methods of applying surfactants are described in U.S. Pat. Nos. 4,950,254 and 5,009,563, both issued to Thomas Osborn, the disclosures of which are hereby incorporated herein by reference. Preferably, however, the surfactant is incorporated into the polymeric resin(s) comprising the topsheet as described in the aforementioned U.S. Pat. No. 4,535,020.

Despite the effective functioning of the surfactant treated prior art fluid-pervious web 40 in topsheet applications for disposable absorbent articles such as sanitary napkins, there can be certain perceived drawbacks associated with topsheets of similar construction. For example, treating the entire exposed surface of the topsheet with a surfactant creates a very wettable surface which, when placed into contact with the wearer's skin, may cause the topsheet to stick to the wearer's skin. This in turn may create a hot, sweaty, and/or sticky sensation for the user which may be viewed as less desirable by some users.

In addition, although capillary web structures of the foregoing varieties are effective in transporting fluid, their effectiveness is limited in that such capillary structures can only move fluid once it reaches the interior of the capillaries. Fluid which wets and remains on wearer contacting surfaces contributes to a "wet" tactile feeling or impression, and to the extent that such fluid may be colored or opaque also contributes to a "stained" visual impression. Surface textures naturally occurring in the material of the web or imparted thereto in formation further increase the likelihood that residual fluid will be trapped or retained on the wearer-contacting surface rather than entering capillary structures for transport away from the surface. Thus, surface topographies which contribute to desirable visual and tactile impressions when dry can also tend to retain residual fluid on the exposed surface and thus reduced desirability under in-use conditions.

Figure 2:
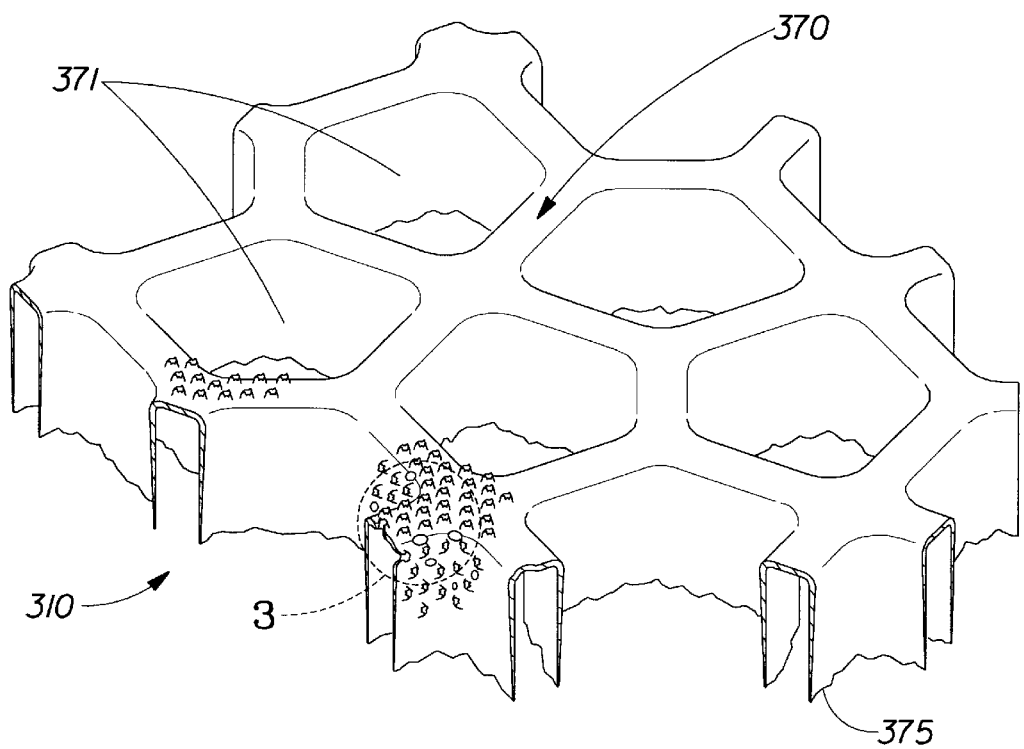
FIG. 2 is a greatly enlarged simplified schematic cross-sectional illustration similar to FIG. 1 of a macroscopically expanded, microscopically apertured three-dimensional web exhibiting a surface energy gradient according to the present invention.

FIG. 2 is an enlarged partially segmented, perspective illustration of a particularly preferred three-dimensional, fluid-pervious formed-film web embodiment of the present invention, generally indicated as 310. The geometrical configuration of the fluid pervious web 310 is generally similar to that of FIG. 1, but including both macro apertures 371 and microapertures 325 (FIG. 3) in accordance with commonly assigned U.S. Pat. No. 4,629,643, issued Dec. 16, 1986 to Curro and Linman, the disclosure of which is hereby incorporated herein by reference.

Figure 3:
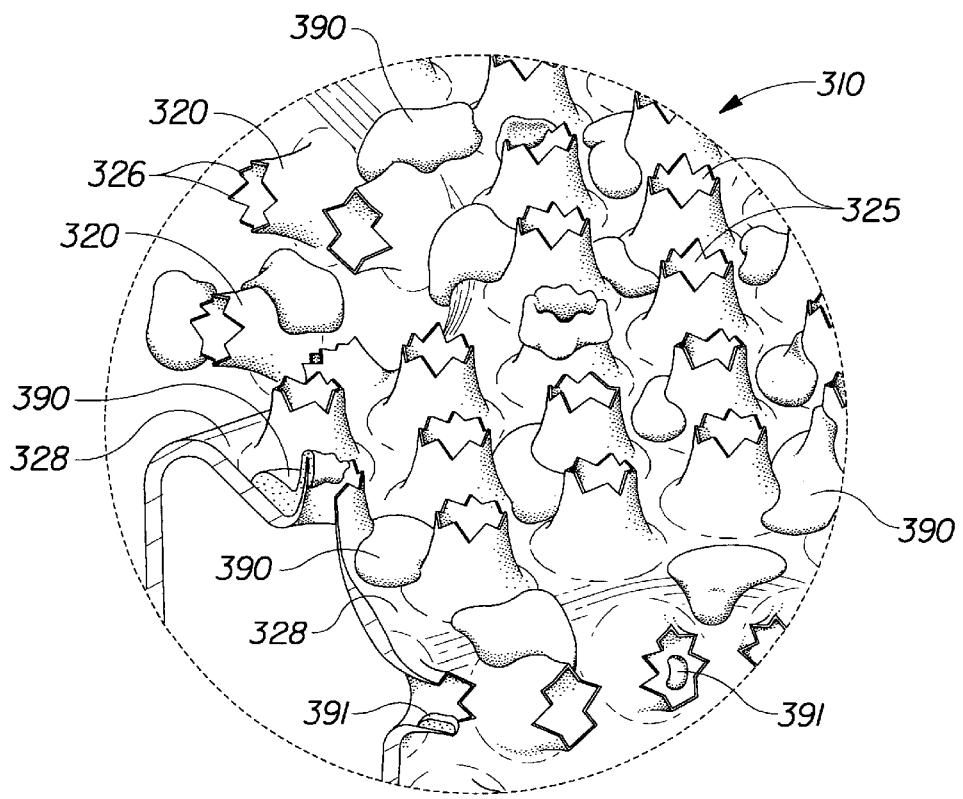
FIG. 3 is a further enlarged, partial view similar to FIG. 6 of the web of FIG. 2.

FIG. 3 is an enlarged partial view of the web of FIG. 2, depicting in greater detail the relationship of the microapertures 325 to the overall web structure. Also depicted in FIG. 3 is the primary undeformed web surface or lands 328 between and around the bases of the microscopic surface aberrations 320, which culminate in microapertures 325 having petals 326. FIG. 3 also depicts the presence of discrete, discontinuous, spaced regions 390 which preferably exhibit a comparatively low surface energy compared with intervening surfaces of the web 328.

The macroapertures 371 provide a primary fluid passageway for transport of bodily fluids from the first or wearer contacting surface 370 to the opposed second surface 375 when the web 310 of the present invention is used as a topsheet for an absorbent article. The microapertures 325 also provide a fluid passageway allowing deposited bodily fluids to move from the wearer contacting surface 370 to the second surface 375. As utilized herein, the term "fluid passageway" is intended to encompass enclosed or at least partially enclosed structures or channels which may communicate fluids. The term fluid passageway is thus intended to encompass the terms "aperture", "channel", "capillary", as well as other similar terms.

A particular benefit of the geometrical configuration of the web 310 of the present invention is the soft and silky tactile impression provided by the structure. As noted above, this geometrical configuration is in accordance with commonly assigned U.S. Pat. No. 4,269,643 which describes microapertured polymeric webs exhibiting a substantially uniform soft and silky tactile impression on at least one of the surfaces. It is believed that this improved tactile response is due at least in part to the reduced resistance of the webs of U.S. Pat. No. 4,269,643 to collapse when compressive or shear forces are applied to the uppermost surface of the web. This reduced resistance to collapse has been found to result in increased potential rewetting because of the increased tendency to contact underlying structure when such webs are used as a topsheet compared to webs having greater structural resistance as are described in, for example the aforementioned U.S. Pat. Nos. 4,342,314 and 4,463,045. In other words, while the preferred prior art web has an improved tactile response, it becomes less efficient than other prior art webs in one aspect of fluid handling. It has been found that this deficiency can be substantially overcome by providing at least the wearer contacting surface 370 of the web 310 with microscopic depositions 390 of a material having a lower surface energy than the underlying polymeric material comprising the bulk of the structure of the web 310.

In accordance with the present invention, regions 390 of the first or wearer-contacting surface 370 of web 310 are less wettable than the lands 328 and other underlying portions of the formed film structure. This difference in wettability, as exemplified by differences in surface energy, is defined herein as a "surface energy gradient."

Figure 5:
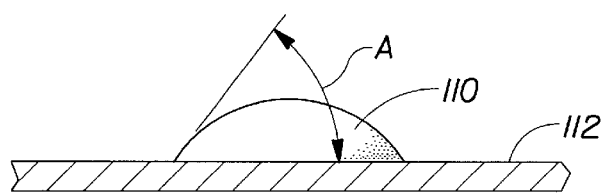
FIG. 5 is an enlarged cross-sectional view of a droplet of liquid on a solid surface, where angle A illustrates the contact angle of the liquid with the solid surface.

A useful parameter of wettability is the contact angle that a drop of liquid (gas-liquid interface) makes with the solid surface (gas-solid interface). Typically, a drop of liquid 110 placed on a solid surface 112 makes a contact angle, A, with the solid surface, as seen in FIG. 5. As the wettability of the solid surface by the liquid increases, the contact angle, A, decreases. As the wettability of the solid surface by the liquid decreases, the contact angle, A, increases. The liquid-solid contact angle may be determined from techniques known in the art, such as those described in greater detail in *Physical Chemistry of Surfaces,* Second Edition, by Arthur W. Adanson (1967), F. E. Bartell and H. H. Zuidema, *J. Am. Chem. Soc.,* 58, 1449 (1936), and J. J. Bikerman, *Ind. Eng. Chem., Anal. Ed.,* 13, 443 (1941), each of which are hereby incorporated herein by reference. More recent publications in this area include Cheng, et al., *Colloids and Surfaces* 43:151–167 (1990), and Rotenberg, et al., *Journal of Colloid and Interface Science* 93 (1): 169–183 (1983), which are also hereby incorporated herein by reference.

As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. This is discussed in detail in the American Chemical Society publication entitled *Contact Angle, Wettability and Adhesion,* edited by Robert F. Gould (Copyright 1964), which is hereby incorporated herein by reference. A surface is said to be wetted by a fluid (hydrophilic) when the fluid tends to spread spontaneously across the surface. Conversely, a surface is considered to be "hydrophobic" if the fluid does not tend to spread spontaneously across the surface.

The contact angle depends on surface heterogeneities (e.g., chemical and physical properties, such as roughness), contamination, chemical/physical treatment of or composition of the solid surface, as well as the nature of the liquid and its contamination. The surface energy of the solid also influences the contact angle. As the surface energy of the solid decreases, the contact angle increases. As the surface energy of the solid increases, the contact angle decreases.

The energy required to separate a liquid from a solid surface (e.g., a film or fiber) is expressed by equation (1):

$$W=G(1+\cos A) \quad (1)$$

where:

W is the work of adhesion measured in erg/cm$^2$,

G is the surface tension of the liquid measured in dyne/cm, and

A is the liquid-solid contact angle measured in degrees. With a given liquid, the work of adhesion increases with the cosine of the liquid-solid contact angle (reaching a maximum where the contact angle A is zero).

Work of adhesion is one useful tool in understanding and quantifying the surface energy characteristics of a given surface. Another useful method which could be utilized to characterize the surface energy characteristics of a given surface is the parameter labeled "critical surface tension", as discussed in H. W. Fox, E. F. Hare, and W. A. Zisman, *J. Colloid Sci.* 8, 194 (1953), and in Zisman, W. A., *Advan. Chem. Series No.* 43, Chapter 1, American Chemical Society (1964), both of which are hereby incorporated herein by reference.

Illustrated below in Table 1 is the inverse relationship between contact angle and work of adhesion for a particular fluid (e.g., water), whose surface tension is 75 dynes/cm.

TABLE 1

| A (degrees) | cos A | 1 + cos A | W (erg/cm$^2$) |
|---|---|---|---|
| 0 | 1 | 2 | 150 |
| 30 | 0.87 | 1.87 | 140 |
| 60 | 0.5 | 1.50 | 113 |
| 90 | 0 | 1.00 | 75 |
| 120 | −0.5 | 0.5 | 38 |
| 150 | −0.87 | 0.13 | 10 |
| 180 | −1 | 0 | 0 |

As depicted in Table 1, as the work of adhesion of a particular surface decreases (exhibiting a lower surface energy of the particular surface), the contact angle of the fluid on the surface increases, and hence the fluid tends to "bead up" and occupy a smaller surface area of contact. The reverse is likewise true as the surface energy of a given surface decreases with a given fluid. The work of adhesion, therefore, influences interfacial fluid phenomena on the solid surface.

Figure 6:
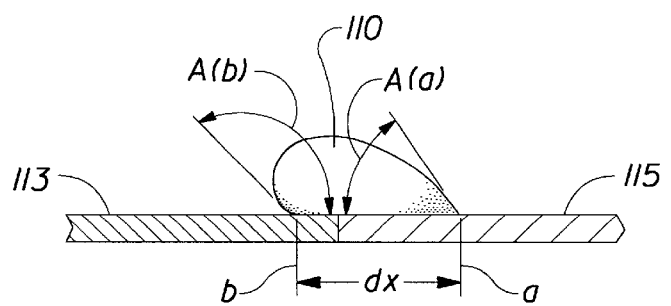
FIG. 6 is an enlarged cross-sectional view of a droplet of liquid on a solid surface having two different surface energies, thus exhibiting two different contact angles A(a) and A(b)

More importantly, in the context of the present invention, differences in surface energy (i.e., surface energy gradients) have been found to be useful in promoting reduced rewet. FIG. 6 illustrates a droplet of fluid 110 which is located on a solid surface having two regions 113 and 115 having differing surface energies (indicated by the different cross-hatching for illustrative purposes). In the situation illustrated in FIG. 6, region 113 exhibits a comparatively lower surface energy than region 115, and hence a reduced wettability for the fluid of the droplet than region 115. Accordingly, the droplet 110 produces a contact angle A(b) at the edge of the droplet contacting region 113 which is greater than the contact angle A(a) produced at the edge of the droplet contacting region 115. It should be noted that although for graphic clarity the points "a" and "b" lie in a plane, the distance "dx" between points "a" and "b" need not be linear, instead representing the extent of droplet/surface contact regardless of the shape of the surface. Droplet 110 thus experiences a surface energy imbalance and hence an external force due to the differences in the relative surface energies (i.e., the surface energy gradient) between regions 113 and 115, which can be represented by the equation (2):

$$dF=G[\cos A(a) -\cos A(b)]dx \quad (2)$$

where:

dF is the net force on the fluid droplet, dx is the distance between the reference locations "a" and "b", G is as defined previously, and A(a), and A(b) are the contact angles A at locations "a" and "b", respectively.

Solving equation (1) for cos A(a) and cos A(b) and substituting into equation (2) yields equation (3):

$$dF =G[(W(a)/G-1)-(W(b)/G-1)]dx \quad (3)$$

Equation (3) can be simplified to equation (4):

$$dF=(W(a)-W(b))dx \quad (4)$$

The importance of the differential in surface energy between the two surfaces is clearly depicted in equation (4), as is the directly proportional effect that changes in the magnitude of the differential in work of adhesion would have on the magnitude of the force.

More detailed discussions of the physical nature of surface energy effects and capillarity may be found in *Textile Science and Technology*, Volume 7, *Absorbency*, edited by Portnoy K. Chatterjee (1985), and *Capillarity, Theory and Practice, Ind. Eng. Chem.* 61,10 (1969) by A. M. Schwartz, which are hereby incorporated herein by reference.

Accordingly, the force experienced by a droplet will cause movement in the direction of the higher surface energy. For simplicity and graphic clarity, the surface energy gradient has been depicted in FIG. 6 as a single, sharp discontinuity or boundary between well-defined regions of constant but differing surface energy. Surface energy gradients may also exist as a continuous gradient or a step-wise gradient, with the force exerted on any particular droplet (or portions of such droplet) being determined by the surface energy at each particular area of droplet contact.

Also, as used herein the terms "capillary" and "capillarity" are used to refer to passageways, apertures, pores, or spaces within a structure which are capable of fluid transport in accordance with the principles of capillarity generally represented by the Laplace equation (5):

$$p=2G(\cos A) /R \quad (5)$$

where:

p is the capillary pressure;

R is the internal radius of the capillary (capillary radius); and

G and A are as defined above.

As noted in *Penetration of Fabrics* by Emery I. Valko, found in Chapter III of *Chem. Aftertreat. Text.* (1971), pp. 83–113, which is hereby incorporated herein by reference, for A =90°, the cosine of A is zero and there is no capillary pressure. For A>90°, the cosine of A is negative and the capillary pressure opposes the entry of fluid into the capillary. Hence, the capillary walls must be of a hydrophilic nature (A<90°) for capillary phenomena to occur. Also, R must be sufficiently small for p to have a meaningful value, since as R increases (larger aperture/capillary structure) the capillary pressure decreases.

Perhaps at least as important as the presence of surface energy gradients is the particular orientation or location of materials having differing surface energies with respect to the orientation and location of the capillaries or fluid passageways themselves. More particularly, materials having a relatively low surface energy are disposed in relation to the capillaries such that fluid deposited on the first or upper surface typically contacts at least one region having a relatively low surface energy and thus experiences the driving force accompanying the gradient. Since the regions having a relatively low surface energy are preferentially disposed on the first surface 370 of the web 310 of the present invention and the underlying polymeric film has a higher surface energy, fluids at a capillary entrance experience a Z-direction driving force to drive the fluid into the capillary where capillary forces can cooperate with the surface energy forces to move the fluid away from the first surface.

Figure 7A:
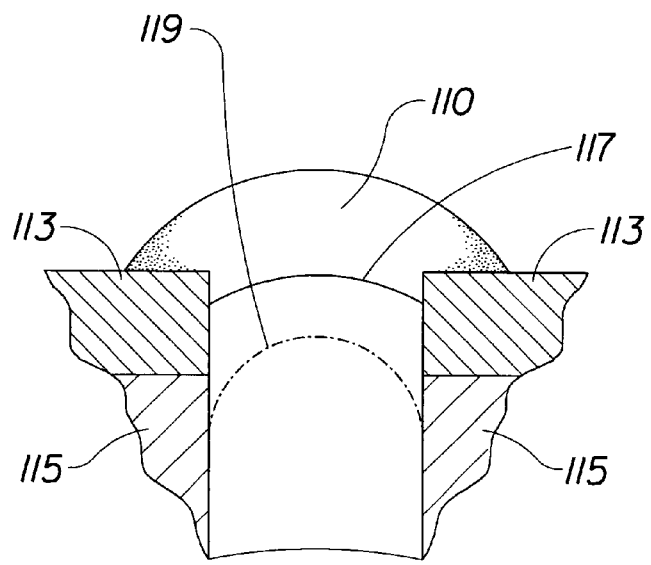
FIGS. 7a and 7b are enlarged cross sectional views of a droplet of liquid located adjacent a generic capillary exhibiting a surface energy gradient.

By way of further explanation of this principle, FIG. 7a depicts a droplet 110 of a fluid which is located over a generic capillary or fluid passageway. This representation is intended to be sufficiently generic as to represent the concept expressed herein without being limited to a particular web material, design, or construction. Analogously to FIG. 6, the capillary is formed so as to present surfaces 113 and 115 having different surface energies (indicated by the different cross-hatching for illustrative purposes). As in FIG. 6, the surface energy of surface 113 is at a predetermined level which is comparatively low in comparison with that of surface 115. Accordingly, the droplet edges in contact with surface 113 will exhibit a relatively larger contact angle A such that the droplet edges make a sharp departure from the interface with surface 113. Surface 115, on the other hand, has a comparatively higher surface energy in comparison with surface 113.

In the situation depicted in FIG. 7a, the droplet 110 is located over and extends partially into the entrance of the capillary. The lower portion of the droplet which is within the capillary forms a meniscus 117, with its edges in contact with the capillary wall in the region 113 having relatively low surface energy. The surface energy gradient between surfaces 113 and 115 is particularly determined so as to contact the lower portion of the droplet in the vicinity of the edge of the meniscus 117. The orientation of the droplet and depth of the meniscus of the droplet are determined by such factors as fluid viscosity, fluid surface tension, capillary size and shape, and the surface energy of the upper surface and capillary entrance.

At the instant when the droplet positions itself over the capillary entrance and the lower edge of the droplet is exposed to the surface energy gradient between surfaces 113 and 115, the meniscus 117 becomes much more concave, such as meniscus 119 depicted in dot-dash line form. When the meniscus changes to a more concave form, such as meniscus 119, the fluid wets the capillary wall in the vicinity of the upper region of relatively high surface energy, surface 115, and the fluid experiences an external force due to the surface energy differential described above in equation (3). The combined surface energy and capillary pressure forces thus act in concert to draw the fluid into the capillary for capillary fluid transport away from the first surface. As the fluid droplet moves downward into the capillary, the comparatively low surface energy nature of the surface 113 at the upper region of the capillary minimizes the attraction of the fluid to the upper surface, reducing the incidence of fluid hang-up or residue on or near the upper surface.

Figure 7B:
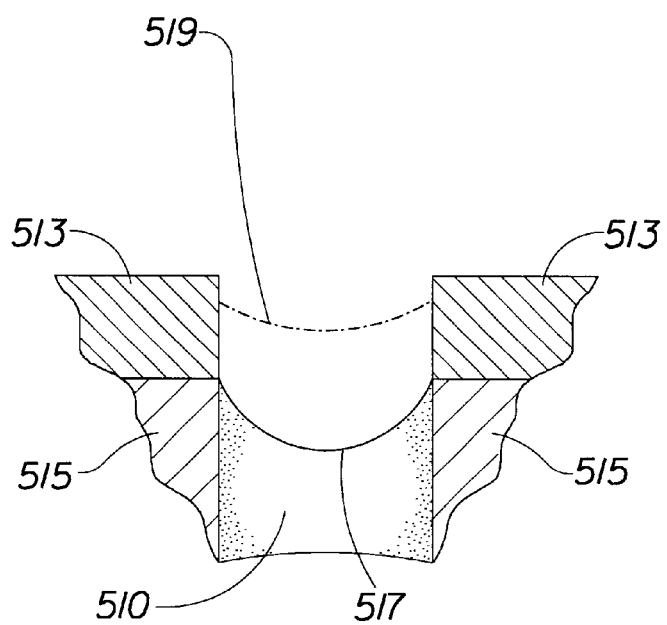

One of skill in the art will also recognize (FIG. 7b) that the surface energy gradient between surfaces 515 and 513 is predisposed to provide an energy barrier to fluid flow from surface 115 toward surface 513 as may cause rewetting when the web 310 of the present invention is used as a topsheet. This situation is the inverse of the situation described above and is depicted in FIG. 7b. That is, when fluid 510 approaches the interface between surface 515 that has a relatively high surface energy and surface 513 that has a relatively low surface energy, the meniscus 517 becomes less concave (shown in dashed form by meniscus 519) indicating the energy barrier provided by the surface energy gradient between surfaces 513 and 515 which impedes flow toward surface 513.

Water is used as a reference liquid throughout only as an example for discussion purposes, and is not meant to be limiting. The physical properties of water are well-established, and water is readily available and has generally uniform properties wherever obtained. The concepts regarding work of adhesion with respect to water can easily be applied to other fluids such as blood, menses and urine, by taking into account the particular surface tension characteristics of the desired fluid.

Referring to FIGS. 2 and 3, while regions 390 of the first or wearer-contacting surface 370 of web 310 have a relatively low surface energy and a relatively low work of adhesion for a given fluid (e.g., water, or bodily fluids such as menses), the lands 328 of the web 310 preferably have a relatively high surface energy and a relatively high work of adhesion for a given fluid. Since the lands 328 of the web 310 have a relatively higher surface energy as compared to the regions 390, the lands 328 are more wettable than the regions 390.

The second surface 375 of the web 310 preferably has a higher overall surface energy and a higher work of adhesion for fluid than that of the first surface 370. The surface energy and work of adhesion for fluid of second surface 375 may be the same as that of the lands 328.

By having a web with a surface energy gradient formed by structures creating regions 390 having a relatively low surface energy adjacent to regions having a higher surface energy (i.e. lands 328) on the surface that is placed adjacent to and in contact with the wearer's skin (i.e., the first surface 370), and a relatively higher surface energy portion located away from contact with the wearer's skin (i.e., the second surface 375), the web 310 will be capable of moving a drop of liquid from the portion of the web exhibiting the relatively lower surface energy to the portion of the web exhibiting the relatively higher surface energy. Likewise, fluid trying to move in the opposite direction will be less able to do so. The motion of the drop of liquid is induced by the surface energy differential between the lower surface energy portions and the higher surface energy portions which results in an imbalance in surface forces acting on the solid-liquid interface. It is believed that this resulting surface energy gradient enhances the fluid handling properties of the web 310 of the present invention and makes the web well suited for use as a topsheet on an absorbent article, such as topsheet 22 on absorbent article 20 illustrated in FIGS. 11 and 12.

In addition to the enhanced fluid handling properties, by designing the web so that its relatively lower surface energy portion can be placed in contact with the wearer's skin, the adhesion between the skin and the web is reduced by decreasing the capillary force generated by occlusive body fluids located between the first surface of the web and the wearer's skin. By providing a structure with reduced adhesion between the wearers skin and the web, the sensation or impression of stickiness associated with adhesion to a plastic web topsheet is also reduced.

As noted above, the potential for rewet is also reduced by having a topsheet with a surface energy gradient according to the aforementioned description. As use forces tend to force the collected fluid to rewet or be squeezed out of the pad (e.g., squeezed by compression from the absorbent core towards the first surface of the topsheet), such undesirable movement will be resisted by the first surface of the topsheet which has a relatively low surface energy to repel the fluid as it attempts to make its way out of the pad through the openings in the topsheet.

While many structures in the prior art have attempted to utilize various superficial coatings to impart greater hydrophobicity and/or reduced coefficient of friction to the overall upper surface of a web, such coatings typically substantially reduce if not eliminate topographical surface features, such as microapertures 325, present in the uncoated web. As discussed above, such surface features are an important physical feature with regard to visual and tactile impression. Moreover, such coatings typically have a smooth, glossy finish which accentuates the sweaty, sticky, plastic-like feel of such webs.

Without wishing to be bound by theory, surface topography is believed to play a major role in not only reducing the negative visual and tactile impressions normally associated with such webs, but also in the handling and/or transport and retention of bodily fluids. Accordingly, fluid pervious webs according to the present invention preferably are constructed so as to preserve the physical surface topography of the initially formed web, i.e., wherein the surface features survive the gradient-generating process.

Figure 4:
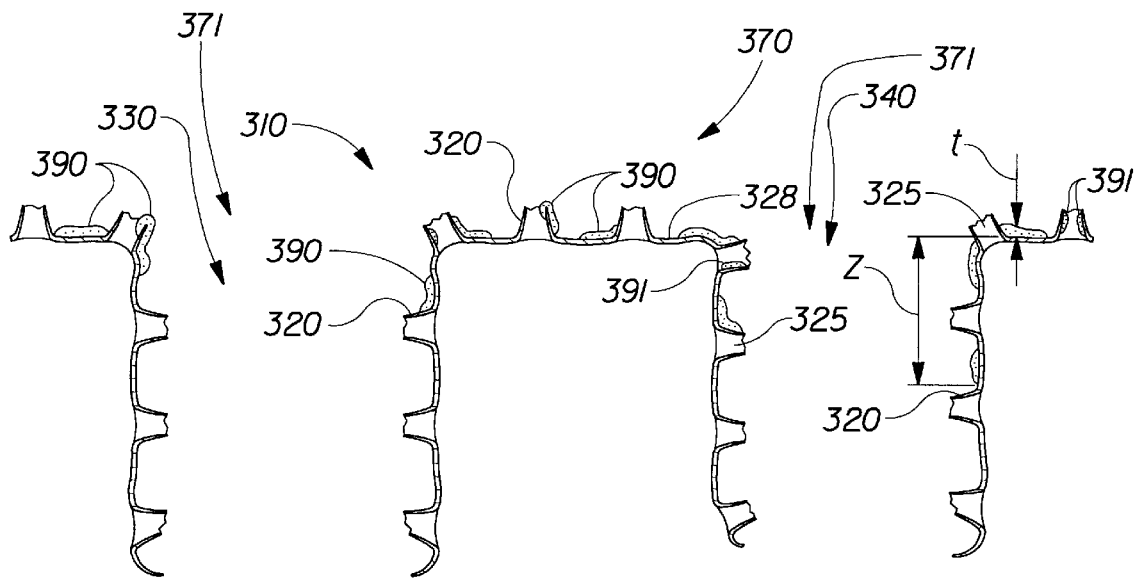
FIG. 4 is an enlarged, cross-sectional view of the web of FIGS. 2 and 3, but showing in greater detail the orientation of the surface energy gradients in relation to the web.

FIG. 4 is an enlarged, cross-sectional view of the web of FIGS. 2 and 3, showing in greater detail the orientation of the regions 390 or low surface energy in relation to other elements of the web 310. As can be seen in FIGS. 3 and 4, regions 391 penetrate below the first surface 370 of the web and down into the macroapertures 371. FIG. 4 also depicts different levels or degrees of penetration of the regions 390 into the macroapertures 371 of the web. For example, macroaperture 330 exhibits comparatively little penetration below the first surface 370 of the web and macroaperture 340 exhibits a greater degree of penetration. Preferably, regions 390 are concentrated near the first surface 370 and decrease in frequency (increase in spacing) with increasing distance from the first surface, such that more low surface energy regions are positioned at or near the first surface 370 for greater effect on fluids on or near the first surface. On average, therefore, the upper regions of the web near the first surface 370 would exhibit a lower average surface energy than that exhibited by lower regions of the web nearer to the second surface 375.

Note also in FIG. 4 the depiction of the thickness "t" of the surface energy treatment used to generate regions 390, and the depth "Z" to which any particular region 390 extends below the first surface 370 of the web. The thickness "t" is preferably small in relation to the depth or extent "Z" of the regions 390 so as to minimize the impact of the generation of the regions on the topography of the web. In a case where the regions 390 are formed by a coating, the thickness "t" is the thickness of the coating.

At each interface between a region 390 and a land 328, a droplet contacting both surfaces experiences a driving force which imparts some degree of motion to the fluid and reduces the likelihood of fluid stagnation or hang-up, particularly on surface topography. Although the regions 390 could be applied in a predetermined pattern, the regions 390 are preferably randomly oriented on the web surfaces, with the randomness increasing the likelihood that the regions of low surface energy 390 will be properly positioned so as to affect any particular droplet or quantity of fluid. Randomness is desirable not only across the first surface 370 of the web, but also within the fluid passageways (e.g. macroapertures 371) themselves. Accordingly, any particular capillary or passageway may exhibit multiple interfaces defined by regions 390 which may also be located at differing locations in the Z-direction from the first surface 370. Also, particular fluid passageways may exhibit more or less regions 390 than other fluid passageways, and regions 390 may also be located so as to entirely reside within fluid passageways (i.e., be entirely located between the first and second surfaces 370, 375 ).

The regions 390 are also preferably discontinuous in nature with respect to the surface directionality of the web. Particularly evident in FIG. 4 is that the surface treatment is preferably discontinuous with respect to the land regions 328 of the web between successive macroapertures 325. The discontinuity of low energy surface treatment depositions applied to a less hydrophobic (or more hydrophilic) substrate such as the web surface results in a pattern of microscopic regions of differing surface energy in the plane of the surface. Such microscopic regions are to be distinguished from large-scale X-Y regions of a zonal nature by their smaller relative size vis-a-vis average droplet size and size of web surface details. Accordingly, as used herein the term "small-scale" is intended to refer to surface features, topography, or regions of low surface energy which are smaller in magnitude than the average size of a droplet of fluid on the surface in question. Average droplet size is a readily determinable characteristic which may be obtained from empirical observations for given fluids and surfaces. As a point of reference, for webs such as depicted in FIG. 2, average droplet sizes for a typical test fluid, as would be applied when conducting the Drop Acquisition test described in the ANALYTICAL METHODS section below, are typically sufficiently large as to cover at least 2–3 individual macroapertures upon initial contact (before acquisition).

Without wishing to be bound by theory, improvements in fluid handling, in particular minimization of rewet, are believed to be facilitated by insuring that the upper surfaces of the web are an energetically less desirable location for such fluids to reside. However, consideration must also be given to facilitating at least some controlled fluid flow on the surface. (One of skill in the art will recognize that, in the absence of external forces, an aqueous fluid that is deposited on a hydrophobic surface will not spontaneously spread to any substantial degree thereon.) Therefore, it is believed to be desirable for the initial fluid contacting surface of the web to facilitate small-scale movement of fluid (as opposed to larger lateral movement across the web surface) toward the nearest available capillary and then rapidly downward into the underlying structure. The present invention is believed to provide both the desired Z-direction driving force (transport through fluid passageways in the web), as well as the X-Y driving force to impart the desired small-scale fluid movement of fluid toward such passageways. Likewise, the same forces tend to minimize flow in the opposite direction, thereby minimizing rewet.

While surface energy gradients of the type herein described could advantageously be employed on non-capillary structures, including the surfaces of such structures as two-dimensional ("planar") films, in accordance with the present invention, it is preferable to employ both small scale X-Y surface energy gradients and small scale Z-direction surface energy gradients of the type herein described to achieve maximum disturbance of fluid and droplet equilibrium and thus minimize fluid residence time and hang-up or residue on the upper regions of the web. Accordingly, the presence of regions 390 may be limited to the first surface of the web, and hence provide X-Y functionality, or limited to the interior of the fluid passageways, but is preferably employed to best advantage both on the first surface of the web and within the fluid passageways.

Accordingly, in capillary web structures of the present invention the surface energy gradients provide a synergistic effect in combination with the capillary nature of the structure to provide enhanced fluid transport and handling characteristics. Fluid on the first surface of the web encounters two differing, complementary driving forces in its journey away from the first surface and toward the second or opposing surface of the web, and typically further onward into the interior of the absorbent article. These two forces likewise combine to oppose fluid movement toward the first surface of the web, thus reducing the incidence of rewet and increasing the surface dryness of the web.

By way of a representative illustration of the synergism of the present invention vis-à-vis the combination or superposition of capillary and surface energy effects, capillary webs according to the present invention have been found to exhibit a unique combination of properties viewed as important from a consumer perspective. More particularly, capillary webs according to the present invention have been found to exhibit good acquisition and dryness characteristics shortly after manufacture of the web and to maintain such characteristics for so as to provide a long shelf life.

In general, acquisition is a reflection of the degree to which the fluid transport web does or does not interfere with fluid pass-through. Improved acquisition rates/times reflect little interference or impedance of fluid pass-through, as well as actual influence of fluid driving forces such as capillarity and surface energy gradients. Dryness is a reflection of the degree to which the fluid transport structure resists fluid transport in the opposite direction, in essence, the degree to which the structure acts as a one-way valve for fluid flow in a preferential direction. In another aspect, dryness is also a measure of how much fluid remains on the surface of the web when the fluid has substantially passed through the web.

Typically, as surface energy of a given capillary web structure decreases uniformly the dryness at the surface improves at the expense of a reduction in acquisition characteristics. Conversely, improvements in acquisition realized by a uniform increase in surface energy of a given capillary web structure are typically offset by reduced dryness characteristics. By utilizing the surface energy gradient principles of the present invention, wherein the surface energy of a portion of the upper surface is decreased while the surface energy of the underlying polymeric structure remains higher, and particularly with the preferred relationship between the high and low surface energy portions, a particularly desirable balance between acquisition and dryness may be obtained without substantial sacrifices in the other parameter. Suitable analytical or test methods for determining web performance with regard to these attributes are described in greater detail in the ANALYTICAL METHODS section below.

A number of physical parameters should be considered in designing a web according to the present invention, more particularly with regard to appropriately sizing and positioning the surface energy gradients for proper fluid handling. Such factors include the magnitude of the surface energy differential (which depends upon the materials utilized), migratability of materials, bio-compatibility of materials, porosity or capillary size, overall web caliper and geometry, surface topography, fluid viscosity and surface tension, and the presence or absence of other structures on either side of the web.

As noted above providing regions 390 having a relatively low surface energy provides a desirable surface energy gradient to webs 310 of the present invention. In order to provide such a surface energy gradient, a suitable material must be more hydrophobic (e.g. have a lower critical surface tension) than the underlying polymeric material that comprises the bulk of the web 310. For example, a typical material that is formed into the microapertured, macroscopically expanded and/or apertured formed film discussed in the aforementioned U.S. Pat. No. 4,609,518 is polyethylene. Polyethylene has a critical surface tension on the order of 31 dynes/cm. Therefore, to insure a surface energy gradient is provided, a material suitable for use in disposing regions 390 onto a polyethylene surface should have a critical surface tension less than 31 dynes/cm. Materials having a satisfactorily low critical surface tension include silicone materials and fluorocarbons, both of which have a critical surface tension of less than about 25 dynes/cm. One of skill in the art will recognize that if the underlying polymeric film has a higher critical surface tension (e.g. polyester at about 45 dynes/cm a materials having a higher critical surface tension than silicone materials or fluorocarbons (e.g. polyethylene) would be suitable.

An exemplary low surface energy material that is suitable as a surface treatment is a silicone release coating from Dow Corning of Midland, Mich. available as Syl-Off 7677 to which a crosslinker available as Syl-Off 7048 is added in proportions by weight of 100 parts to 10 parts, respectively. Another suitable surface treatment is a coating of a silicone material that can be cured (crosslinked) by exposure to ultraviolet (UV) light. Exemplary materials include a silicone resin UV 9300 and a UV activated photo-initiator UV 9380C as are commercially available from General Electric Company, Silicone Products Division, of Waterford, N.Y. Such materials are blended and then exposed to UV light which initiates the crosslinking reaction. A particularly preferred silicone material for treatment is a blend of silicone resin UV 9400 and UV activated photo-initiator 9380C also available from General Electric which are blended in proportions by weight of 97.5 parts to 2.5 parts respectively.

When such a silicone blend is utilized on a formed film such as depicted in FIGS. 2–4, coating application levels of about 0.2 to about 4.0 grams silicone per square meter of web surface area have performed satisfactorily, although other coating levels may prove suitable for certain applications depending upon the nature of the web material and surface, the characteristics of the fluid, etc. The surface energy of the silicone release coating on the first surface of the apertured formed film is less than the surface energy of the polyethylene intermediate portions which preferably has been subjected to a corona discharge treatment and/or treated with a surfactant.

Other suitable treatment materials include, but are not limited to, fluorinated materials such as fluoropolymers (e.g., polytetrafluoroethylene (PTFE), commercially available under the trade names TEFLON and ZONYL) and chlorofluoropolymers. Other materials which may prove suitable, depending on the critical surface tension of the underlying polymer, for providing regions of reduced surface energy include Petrolatum, latexes, paraffins, and the like, although silicone materials are presently preferred for use in fluid-pervious webs in the absorbent article context.

As noted above, incorporation of a surfactant into the resin composition that is extruded to form the polymeric structure of the formed film webs 40 according to the prior art is particularly desirable. The aforementioned U.S. Pat. No. 4,535,020 lists certain surfactant materials suitable for increasing the hydrophilicity of such formed film webs. Other suitable surfactants are also listed in commonly assigned U.S. Pat. No. 5,792,412, issued to Lee, et al. on Aug. 11, 1998, the disclosure of which is incorporated herein by reference. In either case, such resin incorporated surfactants bloom to the web surface after a time so as to increase the hydrophilicity of that surface. As used herein the term "blooming" is intended to mean the permeation of at least a portion of a first material that has been incorporated into the bulk of a second material from the interior portions of the second material to the surface thereof. The first material is then available to affect some property related to that surface. Examples of materials known to the art that bloom include, as mentioned above, surfactants for increasing the wettability of a surface and slip agents for reducing the co-efficient of friction of a surface. For the foregoing reasons, one of skill in the art will recognize that incorporation of surfactant materials into the resin forming the underlying polymeric structure of the webs 310 of the present invention is also desirable.

However, when surfactants that have successfully increased the hydrophilicity of prior art formed films are used with the low surface energy depositions of the present invention, it has been found that a substantial induction period is required before webs that incorporate such surfactants and are subsequently treated with a low surface energy material become effective in rapid acquisition of bodily fluids when such webs are used as a topsheet in an absorbent article. For example, as shown in Example 1 below, the induction period for a treated web whose underlying polymeric structure incorporates a typical prior art surfactant (Atmer 100 as is available from ICI Surfactants of Wilmington, Del.) to achieve a satisfactory acquisition rate (an acquisition time of less than 5 seconds as measured by the Drop Acquisition Test described in the ANALYTICAL METHODS section below) is more than 100 times longer than webs incorporating the surfactants of the present invention.

While not being bound by theory, the following is believed to provide an explanation of this difference in acquisition. Because fluid handling in an absorbent article requires managing flow of fluids both into (acquisition) and out of (rewet) the article, the webs of the present invention must balance the surface properties of both the surface depositions and the underlying polymeric structure that combine to form the webs of the present invention. As noted above, surface depositions that are lower in surface energy than the underlying polymeric structure help provide a desirable balance of acquisition and rewet. It is well known that commercially available surfactant materials are blends of components having various degrees of surface activity. To become effective in modifying the fluid handling properties of the webs of the present invention, an effective amount of a component having a given degree of surface activity must permeate (bloom) to the surface of the web (i.e., more of a component having lower surface activity is required than would be required for a component having a higher surface activity). However, to insure satisfactory acquisition, it has been found desirable that aqueous fluids be able to spread on even the low surface energy depositions mentioned above.

It is believed that the induction period occurs because the very low surface energy of the deposited material creates a more stringent requirement for surface activity to achieve satisfactory fluid spreading than do the polymeric materials used to form webs suitable for topsheets by the prior art. That is, satisfactory spreading on the underlying polymeric structure can be achieved by either a small amount of a high activity component or a larger amount of a low activity component. As used herein, a surfactant material or surfactant component has "high activity" if a water solution thereof, in a concentration greater than the critical surface tension (CMC), has a surface tension between the critical surface tension of the underlying polymeric structure and the critical surface tension of the low surface energy depositions. However, amounts of low activity components that are effective in enabling spreading on the underlying polymeric structure are not effective in enabling spreading on the low surface energy depositions. It has been found that a limitation of the prior art surfactants is that they comprise a mixture of fast blooming, low activity components and slow blooming high activity components. It is also possible that a prior art surfactant comprises an insufficient amount of high activity components to be effective in increasing the surface energy of the low energy depositions to provide satisfactory spreading thereon. The induction period is the time required for an effective amount of surfactant components to bloom to the surface of the depositions to enable spreading of aqueous fluids thereon. The following discussion provides additional theoretical underpinning to the observed sensitivity of the low energy depositions to surfactant type and provides a basis for understanding the classes of surfactant materials that have been found to be effective for purposes of the present invention.

According to the polymer literature (eg, *Diffusion in Polymers*, J. Crank and G. S. Park, Eds., Academic Press, London (1968); *Polymeric Materials Encyclopedia*, J. C. Salamone, Ed., CRC Press, Boca Raton, (1996); *Kirk-Othmer Concise Encyclopedia of Chemical Technology*, Wiley and Sons, New York (1988)), the permeability coefficient for diffusion through a polymer can be written as:

$$P = DS \qquad (6)$$

where:

S is a solubility coefficient; and

D is a diffusivity coefficient.

These coefficients can be complex functions of many variables, including the physical-chemical nature of the polymers, physical-chemical nature of the penetrants, polymeric thickness, polymer morphology, surface treatments, additives, fillers, temperature and the influence of moisture.

The process of permeation of a penetrant through a polymer involves four steps: 1) absorption of the penetrant into the polymer wall; 2) solubility into the polymeric matrix; 3) diffusion through the wall along a concentration gradient; and 4) desorption from the outer polymer wall. As can be seen from equation 6, permeability depends on solubility as well as the diffusion coefficient, each of which is often independent of the other. Solubility is primarily dependent on polymer-penetrant interactions. Diffusivity is affected by inter-polymer chain attractions, mobility of the chains, and penetrant size.

In the present case (i.e. fluid permeable webs having a surface energy gradient), the penetrant is a surfactant that is suitable for increasing the hydrophilicity of the web and the polymers that the surfactant permeates through are thermoplastic films (e.g. polyethylene) and the microscopically deposited low surface energy material (e.g. a silicone material). To be a suitable surfactant material for purposes of the present invention, an effective amount of active wetting agent components from the surfactant material must be capable of quickly permeating these polymers, without requiring high temperatures and or a long induction period. (As noted above, many commercially available surfactants typically comprise blends of individual components; the individual components each having lesser or greater capability of increasing hydrophilicity.) When an effective amount of an active wetting component permeates to the surface of the thermoplastic film that surface is rendered substantially hydrophilic and the surface energy of the low surface energy depositions is increased somewhat. Thus, using the example of a polyethylene film having depositions of a silicone material, a surface energy gradient is created between the untreated and silicone treated areas of the film. As discussed above such a surface energy gradient provides a force tending to direct fluids deposited on the first surface 370 of the web 310 toward passageways (e.g. macroapertures 371 and microapertures 325 ) for transport toward the second surface 375 and serves to impede flow in the opposite direction.

In order to have a satisfactory permeation rate a surfactant according to the present invention must have satisfactory solubility and diffusion properties in both the underlying polymeric structure forming the bulk of the web 310 and in the material comprising the depositions 390.

The solubility of a surfactant or surfactant component in a polymeric matrix (either the underlying polymeric structure or the low surface energy depositions) is believed to depend on the amount and type of the hydrophobic portion relative to the hydrophilic portion. For nonionic surfactant materials this relationship is often characterized in terms of the hydrophile-lipophile balance (HLB) where lower HLB values are more lipophilic. Thus, it would be predicted that surfactants or surfactant components having the lowest HLB values would be more soluble in a non-polar matrix and permeate faster. Surfactants that act as wetting agents typically have HLB values in the range of ~7 to 9 ("Surfactants and Detersive Systems", *Kirk-Othmer Encyclopedia of Chemical Technology*, Vol. 22, Wiley (1983), p. 362). As a result, the more soluble (low HLB) surfactants or surfactant components may not be as effective in increasing the wettability of a surface.

Diffusion is influenced by factors that include: molecular size, molecular shape, and viscosity. For example, at a given HLB (similar solubility), a surfactant with a bulky hydrophile (e.g., a sorbitan ester) would diffuse more slowly than a surfactant with a more linear hydrophile (e.g. a fatty alcohol ethoxylate).

A surfactant that is suitable for purposes of the present invention must not, after blooming to make both the surface depositions and the underlying polymeric structure so wettable that no surface energy gradient is formed. It is believed that suitable surfactants for the present invention are those that have a surface tension, in water solution at a concentration greater than the CMC for the particular surfactant, that is between the critical surface tension of the low surface energy material and the film material. Using the example of silicone depositions on a polyethylene film surface discussed above, a suitable surfactant would have a surface tension, at a concentration that is greater than the CMC for the surfactant of less than about 25 dynes/cm (silicone materials) and about 31 dynes/cm (polyethylene). In another example of polyethylene depositions on a polyester surface suitable surfactants would have a solution surface tension between about 31 dynes/cm (polyethylene) and 45 dynes/cm (polyester).

Table 2 demonstrates the relationship surfactant surface tension and contact angle difference (an indicator of a surface energy gradient) for an exemplary fast blooming surfactant of the present invention and two prior art surfac tants. Additional data further demonstrating this relationship are given in Example 3.

TABLE 2

| Surfactant | Surface Tension[1] (dynes/cm) | Contact Angle of Surfactant Solution on Substrate | | |
|---|---|---|---|---|
| | | Polyethylene[2] | Silicone[2] | Difference[3] |
| Atmer 100[4] | ~33 | 12° | 50° | 38° |
| Pegosperse 200 ML[5] | ~31 | 12° | 55° | 43° |
| Q2-5211[6] | ~21 | 10° | 13° | 3° |

[1]Concentration is 0.1%, which is ≦ CMC for these surfactants
[2]Critical surface tension Polyethylene = ~31 dynes/cm; silicone ~25 dynes/cm
[3]As can be seen from equation 1 above, the surface energy gradient and the contact angle difference are related.
[4]Prior art: A sorbitan cocoate as is available from ICI Surfactants of Wilmington, DE.
[5]Present Invention: An ethoxylated monolaurate as is available from Lonza, Inc. of Fair Lawn, NJ.
[6]Prior Art: A silicone glycol copolymer as is available from Dow corning of Midland, MI.

As can be seen, both the Atmer 100 and the Pegosperse 200 ML provide a meaningful surface energy gradient which will provide the desirable properties discussed above (It will be remembered that the Atmer 100 is not a fast blooming surfactant according to the present invention). Conversely, while the silicone-based surfactant is fast blooming, it is too effective in lowering surface tension after it blooms and there is essentially no difference in contact angle (and no difference in surface energy gradient) between the silicone surface and the polyethylene surface. Similarly, many other siloxane-based and fluorocarbon-based surfactants as are disclosed by the prior art, (eg the aforementioned EP 683, 260) are also too effective in lowering the surface tension of aqueous liquids to be considered a surfactant according to the present invention. As a result, without the surface energy gradient, the desirable properties discussed above will not be present.

Example 2 compares exemplary surfactants of the present invention and of the prior art which have been evaluated to define these general properties of suitable surfactants.

Table 3 shows both the contact angle and the work of adhesion (see equation 1 above) for water on a typical underlying polymeric structure that is suitable for use as web 310 of the present invention (polyethylene) wherein the surfactant has permeated to the surface to provide the surface energy gradient. As can be seen from the examples below, such surface energy gradients can be provided by fast blooming surfactants according to the present invention or by prior art surfactants after the induction period has elapsed.

TABLE 3

| Surface Composition | Contact Angle (degrees) | W (erg/cm$^2$) |
|---|---|---|
| Polyethylene + surfactant | ~0 | 150 |
| Silicone-coated polyethylene + surfactant | ~40 | 132 |

Because of the presence of surfactant, both the treated and untreated surfaces are hydrophilic, (i.e., the contact angle is less than 90°). The hydrophobic silicone coating becomes relatively hydrophilic, (i.e., the contact angle is ~40°), due to surfactant diffusion through the coating. This is the same reason that the polyethylene becomes hydrophilic and is, in fact, the reason the surfactant is incorporated into the resin. However, a surface energy gradient nevertheless exists between these surfaces that is sufficient to provide advantageous fluid handling properties to the webs as described above. The gradient results because of the different effect the surfactant has on the surfaces of silicone treated and non-treated regions. For reference, in the absence of surfactant, both the polyethylene and silicone-treated polyethylene surfaces are hydrophobic, with a contact angle ~100° and a work of adhesion ~75 erg/cm². As noted above a surface energy gradient of this order of magnitude provides a desirable balance of acquisition rate (Drop Acquisition time less than about 5 seconds when measured according to the Drop Acquisition method described in the ANALYTICAL METHODS section below) and rewet performance (a Wetback value of less than about 40 mg when measured according to the Wetback method described in the ANALYTICAL METHODS section below).

One of skill in the art will recognize that, depending on the specific combination of polymer film material, low surface energy material, and surfactant that are chosen for a particular use, the specific contact angles, works of adhesion and surface energy gradient may differ from this example. However, the same principles apply and all such combinations are within the scope of the present invention.

Preferably, after a suitable surfactant according to the present invention has bloomed to the surface, the regions 390 of the web 310 have a work of adhesion for water in the range of about 40 erg/cm² to about 140 erg/cm², more preferably in the range of about 75 erg/cm² to about 140 erg/cm², and most preferably in the range of about 80 erg/cm² to about 130 erg/cm². Preferably, the remainder of the web surrounding regions 390 (i.e. the underlying polymeric structure) has a work of adhesion for water that is greater than the work of adhesion for the regions 390 and is in the range of about 80 erg/cm² to about 150 erg/cm², more preferably in the range of about 110 erg/cm² to about 150 erg/cm², and most preferably in the range of about 132 erg/cm² to about 150 erg/cm2.

Preferably, the difference in the work of adhesion for water between the regions 390 and the remainder of the web is at least about 5 erg/cm². More preferably, the difference is at least about 10 erg/cm². Still more preferably, the difference is at least about 15 erg/cm². In any event, webs according to the present invention have a difference in work of adhesion for water between the regions 390 and the remainder of the web of less than 100 erg/cm².

A suitable solution surface tension is not the only important parameter for a suitable surfactant according to the present invention. It must also be fast blooming. As noted above, a major issue with respect to prior art surfactant materials has been the time required for the surfactant to bloom to the surface so it becomes effective in increasing the wettability thereof when such surfactants are used in webs that have been treated with a low surface energy material. This induction period limits the utility of such webs for further conversion because the webs are not suitable for use as a topsheet material until they are sufficiently wettable. For example, depending on the season of the year when the film having a surfactant incorporated therein is extruded (One of skill in the art will recognize that blooming is slowed by colder temperatures), this induction period can require as much as several months of storage in an unheated warehouse in the US Midwest in the winter months before the web becomes suitable for further conversion. While heating can accelerate blooming, such heating is commercially undesirable and can have other unpredictable negative impacts on web performance. As used herein, a surfactant is fast blooming if it has a permeation rate through polyethylene, using the permeation test described in the ANALYTICAL METHODS section of less than about 240 hours at 72° F. and 50% relative humidity. Preferably the permeation rate is less than about 100 hours.

In addition, certain particularly preferred surfactant materials have unexpectedly been found to be particularly thermally stable or less volatile than prior art surfactant materials are more compatible with the extrusion processes used to produce fluid permeable webs. For example, when surfactants that are suitable for purposes of the present invention are incorporated into the resin compositions used to extrude such fluid permeable webs, build up on die lips of film extruders is substantially reduced. Also, "smoking" during the extrusion processes is much less evident.

Table 4 compares weight loss on heating to a temperature of 250° C. for several surfactants (both prior art and according to the present invention). Such a temperature is typical of extrusion temperatures for polymeric films and weight loss at this temperature is believed to be an indicator of surfactant thermal stability and the "smoking" that results from volatility and/or a lack of thermal stability.

TABLE 4

| Surfactant | % wt lost at 250° C. |
| --- | --- |
| Atmer 100[1] | 19 |
| Tergitol NP-4[2] | 27 |
| Tergitol NP-9[2] | 2 |
| Neodol 23-3[3] | 64 |
| Neodol 23-5[3] | 34 |
| Neodol 25-7[3] | 16 |
| Neodol 25-9[3] | 11 |
| Ameroxol OE 10[4] | 8 |
| Pegosperse 200ML[5] | 36 |
| Pegosperse 400DL[5] | 4 |
| Pegosperse 400ML[5] | 6 |
| Pegosperse 400MOT[5] | 7 |

[1]Available from ICI Surfactants of Wilmington, DE.
[2]Available from Union Carbide Corp. of Danbury, CT
[3]Available from Shell Chemical company, Houston, TX
[4]Available from Amerchol Corp. of Edison, NJ
[5]Available from Lonza, Inc. of Fair Lawn, NJ.
Suitably, a surfactant loses less than about 40% of its weight on heating to 250° C. Preferably, the weight loss is less than about 20%, more preferably, less than about 15%.

Thus, a suitable surfactant material for purposes of the present invention has a fast blooming time and an aqueous surface tension at a concentration greater than the surfactant CMC between the critical surface tension of the low surface energy depositions and the critical surface tension of the underlying polymeric structure. As can be seen by a review of the permeability discussion above, such fast blooming is facilitated by an appropriate molecular weight range (believed to be between about 300 and about 1000) and a low viscosity at the blooming temperature (surfactants having a viscosity of less than about 250 Centipoise at room temperature have been found to be suitable). Suitable surfactants also have an HLB range that enables bodily fluids to partially spread on the low surface energy depositions and to wet the underlying polymeric structure. Particularly preferred surfactants also have a low weight loss on heating to a temperature suitable for extruding said underlying polymeric structure.

Suitable fast blooming surfactants include the nonionic surfactants having a hydrophobe derived from a saturated and/or unsaturated moiety including: fatty alcohols, alkyl phenol compounds, and/or mono or di fatty esters, each preferably having from about 6 to about 22, more preferably from about 8 to about 18, carbon atoms in a hydrophobic chain, more preferably an alkyl or alkylene chain, and a hydrophilic chain joined thereto that is provided by ethoxylating the active hydroxyl of said hydrophobic chain with $\leq 20$, preferably $\leq 15$, more preferably from about 3 to about 12, and even more preferably from about 5 to about 10, ethylene oxide moieties to provide an HLB of from about 6 to about 16, preferably from about 8 to about 13. Without being bound by theory, it is believed that the linear nature of such ethoxylates allows the polar groups of the hydrophile to be "shielded" as the surfactant permeates through a polymeric matrix by formation of structures analogous to crown ethers whereby the surfactant molecule appears to be less polar in the polymeric matrix than it is in its "extended" condition at an interface. As will be recognized, prior art surfactants, such as sorbitan esters, do not have this shielding capability.

Particularly preferred surfactant materials according to the present invention have a hydrophobe that is substantially saturated. As is well known, unsaturation in a fatty compound can lead to oxidative instability and the formation of undesirable odors. Butter rancidity is an example of such oxidative instability.

Exemplary surfactant materials that are suitable according to the present invention include linear fatty alcohol ethoxylates such as the Neodols as are available from Shell Chemical Co. of Houston, Tex., NEODOL 23-7 and 23-9 are particularly preferred; alkyl phenols having a low degree of ethoxylation (e.g.,~4 to ~8) such as TERGITOL NP-6 as is available from Union Carbide Corp. of Danbury, Conn.; and fatty ester ethoxylates including monoesters such as PEGOSPERSE 200 ML and diesters such as PEGOSPERSE 400 DL as are available from Lonza, Inc. of Fair Lawn, N.J.

More specific details as to the nature of the processes which may be utilized to manufacture the microapertured, macroscopically expanded and/or apertured formed films depicted in FIGS. 2–4 are set forth in commonly assigned U.S. Pat. No. 4,609,518, issued Sep. 2, 1986 to Curro et al., the disclosure of which is hereby incorporated herein by reference. Following manufacture of the microapertured formed films, the surface energy gradient properties of the present invention are imparted to the formed films in the manner described above with respect to FIGS. 2–4. Additional detail regarding a method of treating a fluid pervious web to provide microscopic depositions of a low surface energy material is also provided in copending, commonly assigned, U.S. patent application Ser. No. 08/837,024, filed in the name of Ouellette, et al. on Apr. 11, 1997, the disclosure of which is incorporated herein by reference.

For example to manufacture a web such as web 310 depicted in FIGS. 2–4 having surface energy gradients according to the present invention, a sheet of polyethylene is formed into a microapertured, macroscopically expanded and/or apertured formed film according to the aforementioned U.S. Pat. No. 4,609,518 including blending a suitable surfactant as described above (also using the teachings of the aforementioned U.S. Pat. No. 4,535,020). If desired, the web is then subjected to a corona discharge treatment generally in accordance with the teachings of U.S. Pat. No. 4,351,784 issued to Thomas et al. on Sep. 28, 1982; U.S. Pat. No. 4,456,570 issued to Thomas et al. on Jun. 26, 1984; and U.S. Pat. No. 4,535,020 issued to Thomas et al. on Aug. 13, 1985, the disclosures of each of these patents being incorporated herein by reference. Preferably, the underlying polymeric structure is a multilayer film having the surfactant incorporated into the core layer according the U.S. Pat. No. 5,520,875, issued to Wnuk, et al. on May 28, 1996. Such multilayer films are particularly useful because the surfactant that is incorporated therein is: 1) not washed off and 2) less prone to volatilization when the film is formed into a microapertured, macroscopically expanded and/or apertured formed film. A surface treatment, such as those discussed above having a relatively lower surface energy than the surface energy of the underlying surfactant treated film is then applied to the first surface 370 of the formed film to provide regions 390 in the manned described in the aforementioned U.S. patent application Ser. No. 08/837,024. The surface treatment is preferably cured and the finished web 310 rolled into parent rolls for use in subsequent conversion processes.

Figure 8:
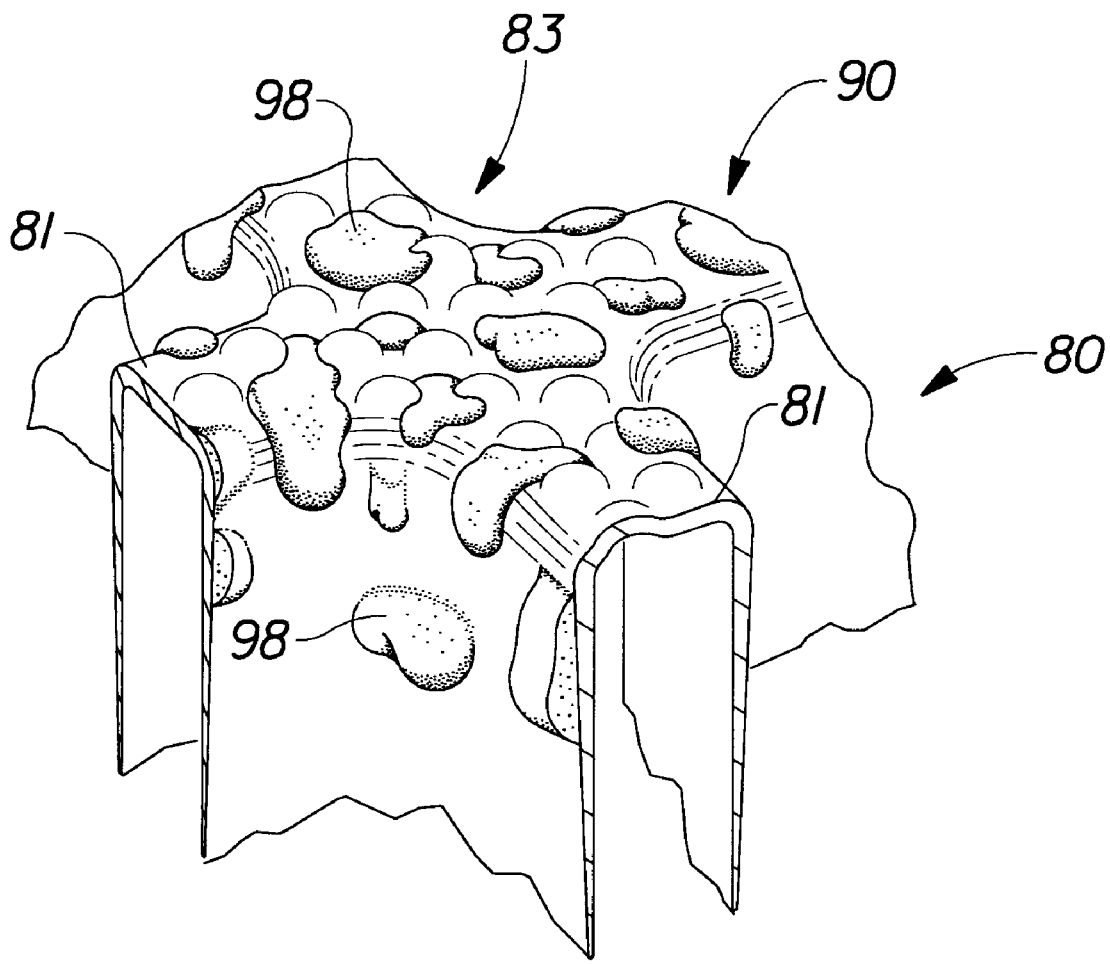
FIG. 8 is a further enlarged, partial view of an alternative web of the present invention similar to FIG. 2 and formed substantially according to U.S. Pat. No. 4,342,314.
Figure 9:
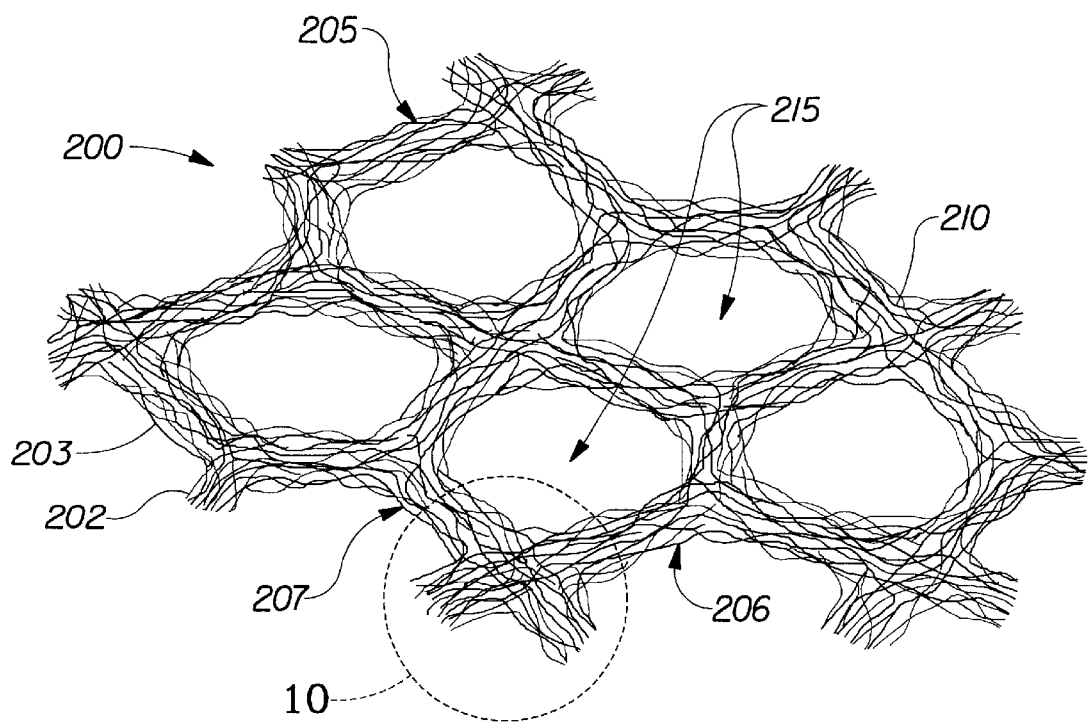
FIG. 9 is an enlarged, partially segmented, perspective illustration of a nonwoven web illustrating another alternative embodiment according to the present invention.
Figure 10:
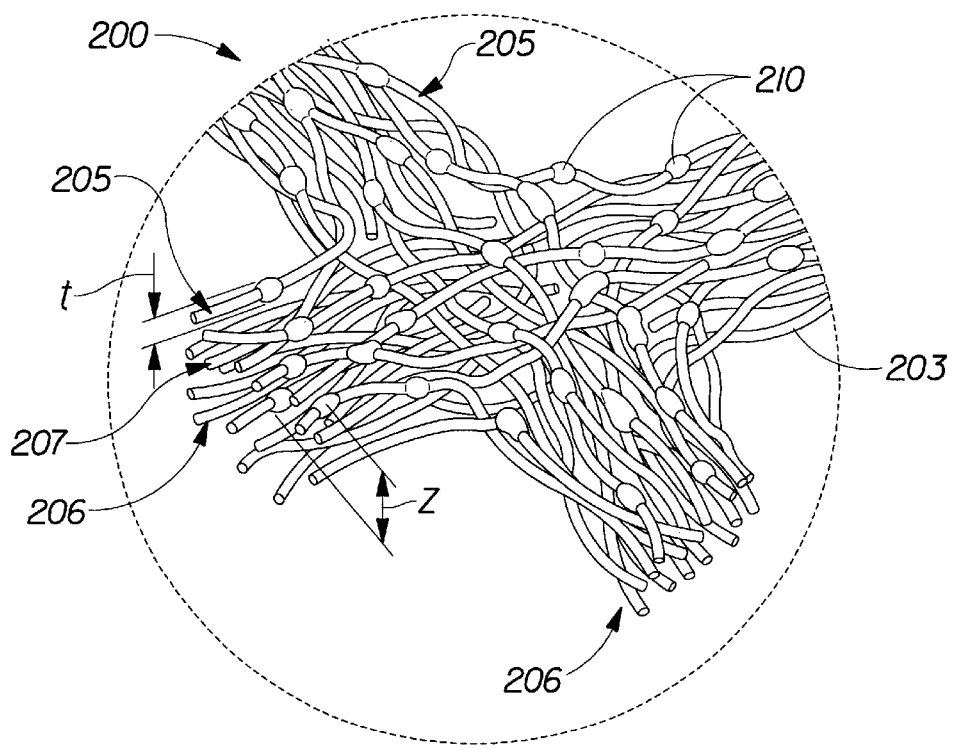
FIG. 10 is a further enlarged, partial view similar to FIG. 8 of the nonwoven web of FIG. 9.

FIGS. 8 to 10 show alternative embodiments of a fluid transport web in accordance with the present invention. These alternative embodiments demonstrate that the fast blooming surfactants described above are efficacious in a wide range of web structures. The key criterion, as noted above, is that the web comprise an underlying polymeric structure having a first surface energy that has disposed thereon microscopic, spaced apart depositions having a second surface energy. Wherein the underlying structure comprises a thermoplastic resinous material with a surfactant incorporated therein which causes the portion of the first surface intermediate the depositions to be substantially hydrophilic.

FIG. 8 is an enlarged partial view of a first alternative embodiment of the present invention where a formed film 80 according to U.S. Pat. No. 4,342,314 has been provided with regions 98 having a relatively low surface energy compared to the surface energy of the underlying polymeric film 81. FIG. 8 depicts the orientation of regions 98 on the first surface 90 and in the film capillaries 83 (similar to the macroapertures 370 of the formed film of FIG. 2). It should be noted that with regard to FIG. 8, as with subsequent figures, the size and shape of regions 98 have been exaggerated in resolution and thickness for graphic clarity. The randomness and irregularity of such depositions or treatments exceed the limitations of graphic depiction, and hence the illustrations herein are intended to be illustrative and not limiting. By way of reference, the surface texture in the form of microscopic aberrations (depicted at 58 in FIG. 1) is (as defined by the Ahr et al. reference) at a microscopic level, and accordingly the relative size, thickness, and extent of the microscopic depositions shown as regions 98 can thus be appreciated.

As noted above the underlying film material 81 has been provided with a fast blooming surfactant according to the present invention. Suitable materials for use in the underlying film 81 are described in the aforementioned U.S. Pat. No. 4,342,314 and a surfactant according to the present invention is incorporated therein according to U.S. Pat. No. 4,535,020. Particularly preferred materials are: polyethylene for the underlying film 81; a silicone for the low surface energy depositions 98; and an ethoxylated mono or di fatty acid ester for the surfactant. Such webs have been found to have a desirable surface energy gradient as discussed above and to be available for conversion into a finished absorbent article without an unacceptably long induction period.

As noted above, the fast blooming surfactants of the present invention are incorporated into the underlying polymeric structure of the underlying film material 81. As will be recognized, such surfactants must be incorporated at a level that is effective in providing the desirable fluid handling properties discussed herein. Suitably, surfactant should be incorporated at a level that is at least about 0.1% by weight of the underlying polymeric structure. Preferably surfactant is incorporated at a level of at least about 0.3% by weight, more preferably at least about 0.75% by weight. Too much surfactant is undesirable because, in excess, surfactant can affect the material and processing properties of the polymeric structure. Suitably, surfactant should be incorporated at a level less than about 5% by weight of the underlying polymeric structure. Preferably surfactant is incorporated at a level of less than about 3% by weight, more preferably less than about 2% by weight. A particularly preferred level according to the present invention is between about 0.75% by weight and about 2% by weight surfactant.

It has also been found that blends of the fast blooming surfactants of the present invention with certain prior art surfactants (surfactants whose solution surface tension is less than the critical surface tension of the low surface energy depositions are unsuitable) also provide the desirable fluid handling properties described herein when used at the above-described ranges for the total amount of the blend. Without being bound by theory, it is believed that permeation of the prior art surfactants is enhanced by the presence of a surfactant according to the present invention. Suitably, a one part of a surfactant blend should comprise between about 0.25 parts of a surfactant according to the present invention so as to provide a blend comprising 0.25 parts of a surfactant of the present invention and 0.75 parts of a prior art surfactant. Preferably, such blends should comprise at least 0.35 parts of a surfactant according to the present invention. A particularly preferred blend comprises equal parts of a surfactant of the present invention and a prior art surfactant.

In a second alternative embodiment, shown in FIGS. 9 and 10, fluid transport web 200 includes a fluid pervious nonwoven web 202 which is preferably comprised of synthetic thermoplastic fibers 203 having a fast blooming surfactant according to the present invention incorporated therein. Suitable fibers include: polyolefin fibers, such polyethylene or polypropylene; polyester; bi-component fibers; and fibers produced from other thermoplastic resins that can be extruded in fibrous form. As noted above, the fibers 203 have a fast blooming surfactant incorporated into the resin composition as the fibers are being extruded. Depending on the desired nonwoven structure, after extrusion the fibers can be cut to staple length for use in forming carded nonwoven materials or finished directly into a nonwoven structure (e. g. melt blown or spunbonded).

The nonwoven web 202 preferably has a first or upper surface 205 and a second surface or lower surface 206. The first surface 205 is spaced from the second surface 206 by an intermediate portion 207. The first surface 205 preferably has a plurality of regions 210 thereon corresponding to regions 390 depicted in FIG. 2. Preferably, the regions 210 exhibit a comparatively low surface energy and preferably comprise a low surface energy surface treatment such as described above with regard to the embodiment of FIGS. 2–4. A plurality of apertures 215 preferably extend from the first surface 205 to the second surface 206 of the nonwoven web 202.

As noted above, the fibers 203 have a fast blooming surfactant incorporated therein. This surfactant behaves in substantially the same manner as described above by blooming to the surface of fibers 203 and through any regions 210 of low surface energy material deposited thereon. Once an effective amount of the surfactant has bloomed to the surface of the fibers 203 and the depositions 210, the surface energy gradient is established and the web can more effectively transport fluids from the first surface 205 to the second surface 206 and impede flow of such fluids in the opposite direction.

Surface treatments for generating regions 210 may be applied to the first surface 205 of the nonwoven web 202 by techniques known in the art such as screen printing, gravure printing, spraying, dip coating, etc. The nonwoven web 200 may be apertured by techniques known in the art such as needle punching, hydroentangling, ring rolling (rolling between interengaged, corrugated rolls), slitting and tentering, embossing, etc.

For configurations wherein the web has defined apertures, the surface treatment 210 is preferably applied to the first surface of the nonwoven web after the aperturing operation is complete. Alternatively, the surface treatment 210 may be applied to the first surface of the nonwoven web prior to the aperturing operation.

As depicted in FIG. 9, the relationship of the regions 210 to the surface topography (including individual fibers protruding upward from the upper surface of the web) is believed to be an important aspect of the present invention. Note the intermittent or discontinuous, spaced nature of the regions with regard to the surface direction of the web and the thickness direction of the web, particularly since the surface treatment as depicted in FIG. 9 is actually a plurality of discrete microscopic particles, droplets, or globules which coat portions of individual fibers rather than a bridging or masking of the fibers which would occlude the interfiber capillaries. As discussed above, this interface between materials results in the surface energy gradient which is believed to be beneficial from a fluid-movement perspective.

Also clearly depicted in FIG. 9 is the penetration of the surface treatment into and below the first surface 205 of the nonwoven web 202. While the majority of the regions 210 are concentrated near the first surface 205 itself, the treated regions extend downward through the web on a fiber-by-fiber basis to achieve a penetration analogous to that defined above with respect to the formed film web. Preferably, regions 210 are concentrated near the first surface 205 and decrease in frequency (increase in spacing) with increasing distance from the first surface. This means that other fluid transport mechanisms (e.g. capillary transport) begin to become controlling in fluid flow from the first surface 205 to the second surface 206 and that there is an energy barrier to rewet similar to that discussed above with respect to the formed film embodiments of the present invention.

Although the foregoing discussion has focused on an apertured nonwoven structure embodiment of the present invention having discrete apertures that are comparatively large in relation to the interfiber spacing, the principles of the present invention are believed to be applicable with equal effect to non-apertured nonwoven structures with sufficient effective porosity to permit the desired fluid pass-through characteristics. This applicability is believed to be due to the non-occlusion of the interfiber capillaries such that sufficient fluid passageways remain open for fluid transmission to the underlying structure. In a structure having discrete apertures comparatively large in relation to the interfiber spacing, non-occlusion is less important but still believed to be advantageous.

In addition, the definition of "fiber" as utilized herein is intended to also encompass a type of fiber structure commonly referred to as a "capillary channel fiber", that is, a fiber having a capillary channel formed therein. Suitable fibers of this variety are described in greater detail in U.S. Pat. Nos. 5,200,248, 5,242,644, and 5,356,405, all of which issued to Thompson et al. on Apr. 6, 1993, Sep. 7, 1993, and Oct. 18, 1994, respectively, the disclosures of which are hereby incorporated herein by reference. Fibrous structures formed of such fibers may exhibit not only inter-fiber capillaries and spaces, but also intra-fiber capillary structures.

Representative Absorbent Article

As used herein, the term "absorbent article" refers generally to devices used to absorb and contain body exudates, and more specifically refers to devices which are placed against or in proximity to the body of the wearer to absorb and contain the various exudates discharged from the body. The term "absorbent article" is intended to include diapers, catamenial pads, tampons, sanitary napkins, incontinent pads, and the like, as well as bandages and wound dressings. The term "disposable" is used herein to describe absorbent articles which are not intended to be laundered or otherwise restored or reused as an absorbent article (i.e., they are intended to be discarded after limited use, and, preferably, to be recycled, composted or otherwise disposed of in an environmentally compatible manner). A "unitary" absorbent article refers to absorbent articles which are formed as a single structure or as separate parts united together to form a coordinated entity so that they do not require separate manipulative parts such as a separate holder and pad.

A preferred embodiment of a unitary disposable absorbent article made in accordance herewith is the catamenial pad, sanitary napkin 20, shown in FIG. 11. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention. It should be understood, however, that the present invention is also applicable to other feminine hygiene or catamenial pads, or other absorbent articles such as diapers, incontinent pads, and the like, as well as other webs designed to facilitate fluid transport away from a surface such as disposable towels, facial tissues, and the like.

It is to be understood that the overall size, shape, and/or configuration of the absorbent article, if any, into which fluid transport webs according to the present invention are incorporated, or utilized in conjunction with, have no criticality or functional relationship to the principles of the present invention. Such parameters, however, must be considered along with the intended fluid and intended functionality when determining appropriate web configurations and appropriate orientation of surface energy gradients according to the present invention.

Sanitary napkin 20 is illustrated as having two surfaces such as first surface 20a, sometimes referred to as a wearer-contacting or facing surface, a body-contacting or facing surface or "body surface", and second surface 20b, sometimes referred to as a garment-facing or contacting surface, or "garment surface". The sanitary napkin 20 is shown in FIG. 11 as viewed from its first surface 20a. The first surface 20a is intended to be worn adjacent to the body of the wearer. The second surface 20b of the sanitary napkin 20 (shown in FIG. 12) is on the opposite side and is intended to be placed adjacent to the wearer's undergarment when the sanitary napkin 20 is worn.

The sanitary napkin 20 has two centerlines, a longitudinal centerline "L" and a transverse centerline "T". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable and refer to a line, axis or direction which lies within the plane of the sanitary napkin 20 that it generally perpendicular to the longitudinal direction. FIG. 11 also shows that the sanitary napkin 20 has a periphery 30 which is defined by the outer edges of the sanitary napkin 20 in which the longitudinal edges (or "side edges") are designated 31 and the end edges (or "ends") are designated 32.

FIG. 11 is top plan view of a sanitary napkin 20 of the present invention in a substantially flat state with portions of the sanitary napkin being cut away to more clearly show the construction of the sanitary napkin 20 and with the portion of the sanitary napkin 20 which faces or contacts the wearer 20a oriented towards the viewer. As shown in FIG. 11, the sanitary napkin 20 preferably comprises a liquid pervious topsheet 22, a liquid impervious backsheet 23 joined with the topsheet 22, an absorbent core 24 positioned between the topsheet 22 and the backsheet 23, and a secondary topsheet or acquisition layer 25 positioned between the topsheet 22 and the absorbent core 24.

The sanitary napkin 20 preferably includes optional side flaps or "wings" 34 that are folded around the crotch portion of the wearer's panty. The side flaps 34 can serve a number of purposes, including, but not limited to helping to hold the napkin in proper position while protecting the wearer's panty from soiling and keeping the sanitary napkin secured to the wearer's panty.

FIG. 12 is a cross-sectional view of the sanitary napkin 20 taken along section line 12—12 of FIG. 11. As can be seen in FIG. 12, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

The topsheet 22 has a first surface 22a and a second surface 22b positioned adjacent to and preferably secured to a first surface 25a of the fluid acquisition layer 25 to promote fluid transport from the topsheet to the acquisition layer. The second surface 25b of the acquisition layer 25 is positioned adjacent to and is preferably secured to the first surface 24a of an absorbent core or fluid storage layer 24 to promote fluid transport from the acquisition layer to the absorbent core. The second surface 24b of the absorbent core 24 is positioned adjacent to and is preferably secured to the first surface 23a of the backsheet 23.

In addition to having a longitudinal direction and a transverse direction, the sanitary napkin 20 also has a "Z" direction or axis, which is the direction proceeding downwardly through the topsheet 22 and into whatever fluid storage layer or core 24 that may be provided. The objective is to provide a substantially continuous path between the topsheet 22 and the underlying layer or layers of the absorbent article herein, such that fluid is drawn in the "Z" direction and away from the topsheet of the article and toward its ultimate storage layer.

The absorbent core 24 may be any absorbent means which is capable of absorbing or retaining liquids (e.g., menses and/or urine). As shown in FIGS. 11 and 12, the absorbent core 24 has a body surface 24a, a garment facing surface 24b side edges, and end edges. The absorbent core 24 may be manufactured in a wide variety of sizes and shapes (e.g. rectangular, oval, hourglass, dogbone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these.

The configuration and construction of the absorbent core may also be varied (e.g., the absorbent core may have varying caliper zones (e.g. profiled so as to be thicker in the center), hydrophilic gradients, superabsorbent gradients or lower density or lower average basis weight acquisition zones; or may comprise one or more layers or structures). The total absorbent capacity of the absorbent core, should, however, be compatible with the design loading and the intended use of the absorbent article. Further, the size and absorbent capacity of the absorbent core may be varied to accommodate different uses such as incontinent pads, pantiliners, regular sanitary napkins, or overnight sanitary napkins.

Exemplary absorbent structures for use as the absorbent core in the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application 0 198 683, the Procter & Gamble Company, published Oct. 22, 1986 in the name Duenk, et al. The disclosures of each of these patents are incorporated herein by reference.

A preferred embodiment of the absorbent core 24 has a surface energy gradient similar to the surface energy gradient of the topsheet 22. The body facing surface 24a of the absorbent core and the portion of the absorbent core 24 immediately adjacent the body facing surface 24a preferably has a relatively low surface energy as compared to the garment facing surface 24b which has a relatively high surface energy. It is important to note that while there is a surface energy gradient within the absorbent core 24, the surface energy of the wearer-contacting or the body facing surface 24a of the absorbent core is preferably greater than the surface energy of the garment facing surface 25b of the acquisition layer 25. This relationship is preferred in order that fluid may be pulled or driven from the acquisition layer into the absorbent core. If the surface energy of the body facing surface 24a of the absorbent core were less than that of the garment facing surface 25b of the acquisition layer fluid in the acquisition layer 25 would be repelled by the absorbent core, thus rendering the absorbent core useless.

The backsheet 23 and the topsheet 22 are positioned adjacent the garment facing surface and the body facing surface respectively of the absorbent core 24 and are preferably joined thereto and to each other by attachment means (not shown) such as those well known in the art. For example, the backsheet 23 and/or the topsheet 22 may be secured to the absorbent core or to each other by a uniform continuous layer of adhesive, a patterned layer of adhesive or any array of separate lines, spirals or spots of adhesive. Adhesives which have been found to be satisfactory are manufactured by H. B. Fuller Company of St. Paul, Minn. under the designation HL-1258, and by Findlay of Minneapolis, Minn., under the designation H-203 1. The attachment means will preferably comprise an open pattern network of filaments of adhesive as disclosed in U.S. Pat. No. 4,573,986 issued to Minetola et al. on Mar. 4, 1986, the disclosure of which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978 and U.S. Pat. No. 4,842,666 issued to Werenicz on Jun. 27, 1989. The disclosures of each of these patents are incorporated herein by reference. Alternatively, the attachment means may comprise heat bonds, pressure bonds, ultrasonic bonds, dynamic mechanical bonds or any other suitable attachment means or combinations of these attachment means as are known in the art.

The backsheet 23 is impervious to liquids (e.g., menses and/or urine) and is preferably manufactured from a thin plastic film, although other flexible liquid impervious materials may also be used. As used herein, the term "flexible" refers to materials which are compliant and are more readily conformed to the general shape and contours of the human body. The backsheet 23 prevents the exudates absorbed and contained in the absorbent core from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet of the polyethylene film having a thickness of from about 0.012 mm (0.5 mil) to about 0.051 mm (2.0 mil). Exemplary polyethylene films are manufactured by Clopay Corporation of Cincinnati, Ohio, under the designation P18-1401 and by Tredegar Film Products of Terre Haute, Ind., under the designation XP-9818. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer or garment facing surface 23b of the backsheet 23 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation 2238. Suitable adhesive fasteners are also described in U.S. Pat. No. 4,917,697. Before the sanitary napkin is placed in use, the pressure-sensitive adhesive is typically covered with a removable release liner 37 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, Wis. The sanitary napkin 20 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps 34 each of which are adjacent to and extend laterally from the side edge of the absorbent core. The flaps 34 are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; and U.S. Pat. No. 4,589,876 entitled "Sanitary Napkin", which issued to Van Tilburg on May 20, 1986. The disclosure of each of these patents is hereby incorporated herein by reference.

In a preferred embodiment of the present invention, an acquisition layer(s) 25 may be positioned between the topsheet 22 and the absorbent core 24. The acquisition layer 25 may serve several functions including improving wicking of exudates over and into the absorbent core. There are several reasons why the improved wicking of exudates is important, including providing a more even distribution of the exudates throughout the absorbent core and allowing the sanitary napkin 20 to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, filed Dec. 17, 1991 in the names of Cree, et al. The disclosures of each of these references are hereby incorporated herein by reference. In a preferred embodiment, the acquisition layer may be joined with the topsheet by any of the conventional means for joining webs together, most preferably by fusion bonds as is more fully described in the above-referenced Cree application.

EXAMPLES

Example 1

This example compares the induction period of a web using a prior art surfactant with the induction period of a web using an exemplary surfactant according to the present invention. In this example the drop time, as measured using the Drop Acquisition Test is measured as a function of time since the web sample was extruded according to the aforementioned U.S. Pat. No. 5,520,875 and treated with a silicone material as described in the aforementioned U.S. patent application Ser. No. 08/826,508. The samples were then aged under controlled temperature and humidity (72° F./50%) The results are shown in Table 5.

TABLE 5

| | Drop Time (Seconds) | | | | | | |
| --- | --- | --- | --- | --- | --- | --- | --- |
| | | | Age of Sample (hrs) | | | | |
| Surfactant | 0.5 | 336 | 504 | 672 | 840 | 1512 | 3024 |
| Prior Art: Atmer 100, 1% | 24 | 9 | 11 | 9 | 7 | 2 | 3 |
| Present Invention: Pegosperse 400DL, 1% | 4 | 0.7 | 0.8 | 0.8 | 1.0 | 0.8 | 1.0 |

The induction period of the surfactant of the present invention to achieve a drop time of less than 5 seconds is at least two orders of magnitude less than the prior art surfactant.

Example 2

This example shows the time required for an amount of surfactant that is effective in lowering the contact angle of water to less than 20° to permeate through a polyethylene film using the Permeation Rate method given in the TEST METHODS section below. The results are shown in Table 6.

TABLE 6

| Surfactant | Time to Reach 20° Contact Angle (or contact angle at longest time) |
| --- | --- |
| Atmer 100[1] | 57° at 264 hrs |
| Atmer 645[1] | 51° at 333 hrs |
| Tergitol NP-4[2] | 8 hrs |
| Tergitol NP-9[2] | 85° at 264 hrs |
| Pluronic L31[3] | 86° at 264 hrs |
| Pluronic L43[3] | 87° at 264 hrs |
| Neodol 23-3[4] | <3 hrs |
| Neodol 23-5[4] | <3 hrs |
| Neodol 25-7[4] | <3 hrs |
| Neodol 25-9[4] | 4 hrs |
| Ameroxol OE 10[5] | 16 hrs |
| Pegosperse 200ML[6] | 20 hrs |
| Pegosperse 400DL[6] | 48 hrs |
| Pegosperse 400ML[6] | ~60 hrs |
| Pegosperse 400MOT[6] | ~40 hrs |
| Dow Corning DC 193[7] | 71° at 333 hrs |
| Q2-5211[7] | 16 hrs |

[1]Available from ICI Surfactants of Wilmington, DE.
[2]Available from Union Carbide Corp. of Danbury, CT
[3]Available from BASF Corp. of Mt. Olive, NJ
[4]Available from Shell Chemical Company, Houston, TX
[5]Available from Amerchol Corp. of Edison, NJ
[6]Available from Lonza, Inc. of Fair Lawn, NJ.
[7]Available from Dow Corning Corp. of Midland, MI

Example 3

This example shows the induction period at 60° C. for surfactant permeation through polyethylene and silicone coated polyethylene (1.2 grams per square meter) as measured by determining the contact angle of water on the surfaces as a function of permeation time. The method used is similar to the Permeation Rate method described in the TEST METHODS section except that the experiment was conducted at 60° C. and that the samples included silicone coated polyethylene. Results are shown in Table 7.

TABLE 7

Contact Angle (Degrees)

Permeation time at 60° C. (hrs)

| Surfactant | Polyethylene | | | | | Silicone-coated Polyethylene | | | | |
|---|---|---|---|---|---|---|---|---|---|---|
| | 0 | 1 | 3 | 24 | 48 | 0 | 1 | 3 | 24 | 48 |
| Atmer 100 | 87 | 54 | 0 | 0 | 0 | 94 | 45 | 54 | 40 | |
| Atmer 100/ Pegosperse 400 DL* | 87 | 0 | 0 | 0 | 0 | 94 | 38 | 38 | 36 | |
| Pegosperse 400 DL | 87 | 0 | 0 | 0 | 0 | 94 | 41 | 36 | 34 | 33 |

*Equal Parts

As can be seen, the induction period (time to reach an equilibrium contact angle of about 0 degrees on polyethylene and about 40 degrees on silicone-coated polyethylene) is very short at 60° C. (<3 hours) in all cases. There is a surface energy gradient (shown by a difference in contact angles of about 40 degrees) between the polyethylene surface and the silicone-coated polyethylene surface for all surfactant systems tested after equilibrium is established.

ANALYTICAL METHODS

Permeation Rate

Overview

This method determines permeation rate and permeation time of a surfactant material through polyethylene film by measuring contact angle as a function of time until the contact angle is lowered to a predetermined value previously defined as indicating suitable wettability.

Test Material

Neat surfactant

Equipment and Solvents

Disposable transfer pipette

Weighing Dishes Smooth 70 mL aluminum as are available from VWR Scientific Products of Cincinnati, Ohio as Catalog Number 25433-089

Pipette, 0–20 µL range (e.g., Eppendorf pipettor)

Pipette, 0–10 mL range (e.g., Eppendorf pipettor)

Environmentally controlled room at 22° C./50% RH

Stopwatch

Goiniometer: A Model 100, available from Rame-Hart of Mt. Lakeside, N.J, has been found to be suitable.

Polyethylene Film: LDPE/LLDPE (~50/50 blend) film containing no $TiO_2$~0.4 mil thick as is available from Tredegar Film Products of Terre Haute, Ind.

Method

The following procedure is performed in a room controlled at 22±1° C. (72±2° F.) and 50±2% RH after conditioning the materials in the same room for at least 1 hour. Control of environmental conditions is important because both temperature and humidity can dramatically affect permeation rates.

Procedure

1. Using a disposable transfer pipette, place neat surfactant into an aluminum weigh boat in a sufficient amount to cover the bottom surface, i.e., ~5 mL to create a surfactant reservoir.
2. Place a sheet of polyethylene film in contact with the surfactant reservoir, ensuring that no air bubbles are present under the film. The film sheet should be large enough so that edges of the film extends at least 1 inch (25 mm) past the upper edge of the weigh boat to prevent surfactant from contaminating the top surface of the film by creeping around the film edges. One film sheet should be used only one time in this method.
3. An ink pen or permanent marker is used to outline the region of the film visually observed to be in contact with the surfactant reservoir in the flat bottom of the weigh boat.
4. Separate the film from the surfactant reservoir after a pre-determined time and place it, surfactant side down, on the stage of the goiniometer so there are no visible wrinkles or bubbles, securing with double-sided tape if necessary.
5. Measure the contact angle on the film surface within outlined area according to the following procedure:
   a) Calibrate the Goiniometer according to the manufacturer's instructions.
   b) Place a 4 µL drop of distilled water carefully onto the surface of the film.
   c) Focus the drop image while looking through the eyepiece.
   d) Adjust the stage height and the numbered wheel on the eyepiece as necessary to align the horizontal crosshair line with the surface of the substrate, keeping the measuring crosshair line at approximate a right angle to the horizontal line.
   e) Adjust the x-y position of the stage so that the extreme left corner of sessile drop is located at the origin of the axes formed by the crosshairs.
   f) Slowly rotate the measuring crosshair line to tangency with the sessile drop. After 2 minutes record the contact angle as the number indicated on the numbered wheel by the mark on the inner wheel used to adjust the measuring crosshair line.
   g) Repeat steps b–f. using at least 2 more drops deposited on the same film piece, being careful to place additional drops on untested (i.e., dry) areas. By checking the contact angle at multiple permeation times, the rate of permeation of surface active components is determined. The time required to achieve a contact angle <20° is taken as the permeation time.

Drop Acquisition

1) Place a sample, approximately 18 cm×28 cm, over one layer of BOUNTY towel (available from Procter & Gamble of Cincinnati, Ohio) on a flat surface. Place a clear Lexan® plate, 15 cm long by 20 cm wide by 1 cm thick, with eighteen 1.9 cm (¾") holes drilled 2.5 cm apart in 3 rows of six holes each, on top of the topsheet sample. The pressure exerted on the topsheet by this plate is ~0.02 psi (0.14 kPa), ensuring intimate contact between the topsheet and the Bounty towel.
2) Deliver a 45 microliter drop of sheep blood from a pipette (A 100 microliter capacity Eppendorf Air Displacement Pipette has been found to be satisfactory) onto the surface of the sample within one of the holes in the plate. The pipette tip should be approximately 3–5 mm above the topsheet surface, and the drops should be applied in such a manner that the force exerted by delivery from the pipette is minimized.
3) Start timing acquisition as soon as the drop contacts the sample.
4) Stop timing when the top surface plane of the sample again becomes visible as a result of the drop passing into or through the sample. Record this drop acquisition time.
5) If the acquisition time exceeds 60 seconds, record the result as 61 seconds.

6) Repeat steps 1 through 5 an additional seventeen times through the remaining holes in the Lexan plate so as to provide eighteen measurements per sample.
7) Repeat steps 1 through 6 on two more topsheet samples.
8) Calculate the mean drop acquisition time, using 61 seconds for those drops which did not pass into or through the sample within 60 seconds.

Wetback

Wetback is a test designed to measure the amount of liquid which emerges from an absorbent structure through a topsheet to cause wetness on the surface of the topsheet. The method used herein is described in European Disposables and Nonwovens Association (Brussels, Belgium) standard method number 151.1-96 with the following differences:

| Test Condition | EDANA Method 151.1- | Method of Present Invention |
| --- | --- | --- |
| Environmental Temperature | 96 | 22 ± 1° C. |
| Environmental Relative Humidity | 20 ± 2° C. | 50 ± 2% |
| Filter Paper Type | 65 ± 2% | Ahlstrom (Mt. Holly Springs, PA) #632 |
| Number of Pieces of Filter Paper | ERT FF3 5 | 7 |
| Confining Pressure | 4000 g/(10 cm)$^2$(~3.9 kPa) | 0.77 psi (5.2 kPa) |
| Test Fluid | | Sheep's Blood |
| Fluid Loading | Synthetic Urine | 7.5 ml |
| Exposure Time: | 3.3 times wt of filter paper | |
| Distribution | | 15 Minutes |
| Rewet | | 15 Seconds |
| | 3 Minutes Under Load 2 Minutes | |

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web having first and second surfaces, said web comprising:
  (a) an underlying polymeric structure, said polymeric structure has a plurality of fluid passageways therethrough placing said first and second surfaces in fluid communication with one another and a surface of the underlying polymeric structure, wherein said underlying polymeric structure comprises a thermoplastic resin, said thermoplastic resin having a first critical surface tension;
  (b) a plurality of microscopic spaced depositions of a low surface energy material on said underlying polymeric structure adjacent said first surface, said low surface energy material has an exterior surface opposite an interior surface which is adjacent to said first surface and a second critical surface tension that is lower than said first critical surface tension; and
  (c) a fast blooming surfactant dispersed in said underlying polymeric structure and in said low surface energy material, wherein said surfactant has a permeation rate less than about 240 hours, a surface tension in aqueous solution that is between said first critical surface tension and said second critical surface tension;
  wherein, after an effective amount of said fast blooming surfactant sufficient to enable spreading of aqueous fluids has permeated to said surface of the underlying polymeric structure and said exterior surface of the low surface energy material, said surface of the underlying polymeric structure has a first surface energy and said exterior surface of the low surface energy material has a second surface energy which is lower than said first surface energy, a difference between said first and second surface energies defining a surface energy gradient which is adapted to exert a force on fluid contacting said first surface, such that said fluid will be directed toward said fluid passageways for transportation away from said first surface and in the direction of said second surface and that flow of said fluid in the opposite direction is impeded.

2. The web of claim 1 wherein said fast blooming surfactant comprises a hydrophobic chain and a hydrophilic chain and is a nonionic material selected from the group consisting of ethoxylated fatty alcohols, ethoxylated alkyl phenols, ethoxylated mono fatty acid esters, ethoxylated di fatty esters, and mixtures thereof.

3. The web of claim 2 wherein said hydrophobic chain has an HLB between about 6 and about 16.

4. The web of claim 2 wherein said hydrophobic chain comprises about 8 to about 18 carbon atoms.

5. The web of claim 4 wherein said hydrophobic chain is substantially saturated.

6. The web of claim 2 wherein said hydrophilic chain comprises less than 12 ethylene oxide moieties.

7. The web of claim 6 wherein said hydrophilic chain comprises less than 10 ethylene oxide moieties.

8. The web of claim 7 wherein said hydrophilic chain comprises between about 5 and about 10 ethylene oxide moieties.

9. The web of claim 2 wherein said surfactant comprises an ethoxylated saturated fatty alcohol.

10. The web of claim 2 wherein surfactant comprises an ethoxylated alkyl phenol.

11. The web of claim 2 wherein said surfactant comprises a ethoxylated saturated mono fatty acid ester.

12. The web of claim 2 wherein said surfactant comprises a ethoxylated saturated di fatty acid ester.

13. The web of claim 2 wherein said surfactant comprises a blend of ethoxylated mono and di fatty esters.

14. The web of claim 1 wherein said permeation rate is less than about 100 hours.

15. The web of claim 1 wherein said web has a low weight loss on heating to a temperature suitable for extruding said underlying polymeric structure.

16. The web of claim 15 wherein said weight loss on heating is less than about 40%.

17. The web of claim 16 wherein said weight loss on heating is less than about 20%.

18. An absorbent article, said absorbent article comprising:
  a liquid permeable topsheet;
  a liquid impermeable backsheet disposed beneath said topsheet and joined thereto at least about a periphery of said absorbent article; and an absorbent core disposed between said topsheet and said backsheet;

wherein said topsheet has first and second surfaces, and comprises:

(a) an underlying polymeric structure said polymeric structure has a plurality of fluid passageways therethrough placing said first and second surfaces in fluid communication with one another and a surface of the underlying polymeric structure, wherein said underlying polymeric structure comprises a thermoplastic resin, said thermoplastic resin having a first critical surface tension;

(b) a plurality of microscopic spaced depositions of a low surface energy material on said underlying polymeric structure adjacent said first surface, said low surface energy material has an exterior surface opposite an interior surface which is adjacent to said first surface and a second critical surface tension that is lower than said first critical surface tension; and (c) a fast blooming surfactant dispersed in said underlying polymeric structure and in said low surface energy material, wherein said surfactant has a permeation rate less than about 240 hours, a surface tension in aqueous solution that is between said first critical surface tension and said second critical surface tension;

wherein, after an effective amount of said fast blooming surfactant sufficient to enable spreading of aqueous fluids has permeated to said surface of the underlying polymeric structure and said exterior surface of the low surface energy material, said surface of the underlying polymeric structure has a first surface energy and said exterior surface of the low surface energy material has a second surface energy which is lower than said first surface energy, a difference between said first and second surface energies defining a surface energy gradient which is adapted to exert a force on fluid contacting said first surface, such that said fluid will be directed toward said fluid passageways for transportation away from said first surface and in the direction of said second surface and that flow of said fluid in the opposite direction is impeded.

19. An absorbent article according to claim 18 wherein said topsheet further comprises a formed film.

20. An absorbent article according to claim 19 wherein said topsheet further comprises a nonwoven material.

* * * * *

UNITED STATES PATENT AND TRADEMARK OFFICE
CERTIFICATE OF CORRECTION

PATENT NO. : 6,353,149 B1
DATED : March 5, 2002
INVENTOR(S) : Keith Joseph Stone It is certified that error appears in the above-identified patent and that said Letters Patent is hereby corrected as shown below:

Column 1,
Line 42, please delete "clothlike" and insert therefor -- cloth-like --.
Line 63, after "itself" please insert -- . -- (a period).

Column 5,
Line 18, after "thereof" please insert -- . -- (a period).

Column 8,
Line 39, please delete "Adanson" and insert therefor -- Adamson --.

Column 12,
Line 63, please delete "wearers" and insert therefor -- wearer's --.

Column 20,
Line 20, please delete "corning" and insert -- Corning --.

Column 21,
Line 37, please delete "150 erg/cm2" and insert therefor -- 150 erg/cm$^2$ --.

Column 22,
Line 39, please delete "company" and insert therefor -- Company --.

Column 29,
Line 62, please delete "H-203 1" and insert therefor -- H-2031 --.

Column 32,
Line 5, please delete "TABLE 5" and insert therefor --

TABLE 5

Drop Time (Seconds)

| Age of Sample (hrs) | 0.5 | 336 | 504 | 672 | 840 | 1512 | 3024 |
|---|---|---|---|---|---|---|---|
| Surfactant | | | | | | | |
| Prior Art: Atmer 100, 1% | 24 | 9 | 11 | 9 | 7 | 2 | 3 |
| Present Invention: Pegosperse 400DL, 1% | 4 | 0.7 | 0.8 | 0.8 | 1.0 | 0.8 | 1.0 |

--(to correct spacing of headings).

UNITED STATES PATENT AND TRADEMARK OFFICE
CERTIFICATE OF CORRECTION

PATENT NO.   : 6,353,149 B1
DATED        : March 5, 2002
INVENTOR(S)  : Keith Joseph Stone It is certified that error appears in the above-identified patent and that said Letters Patent is Column 33,
Line 1, please delete "TABLE 7" and insert therefor --

TABLE 7
Contact Angle (Degrees)

|  | Polyethylene | | | | | Silicone-coated Polyethylene | | | | |
|---|---|---|---|---|---|---|---|---|---|---|
| Permeation time at 60°C (hrs): | 0 | 1 | 3 | 24 | 48 | 0 | 1 | 3 | 24 | 48 |
| Surfactant | | | | | | | | | | |
| Atmer 100 | 87 | 54 | 0 | 0 | 0 | 94 | 45 | 54 | 40 | |
| Atmer 100/Pegosperse 400DL* | 87 | 0 | 0 | 0 | 0 | 94 | 38 | 38 | 36 | |
| Pegosperse 400DL | 87 | 0 | 0 | 0 | 0 | 94 | 41 | 36 | 34 | 33 |

\* Equal Parts

-- (to correct spacing of headings).

Column 35,
Line 18, please delete the table and insert therefor --

| Test Condition | EDANA Method 151.1-96 | Method of Present Invention |
|---|---|---|
| Environmental Temperature | 20±2°C | 22±1°C |
| Environmental Relative Humidity | 65±2% | 50±2% |
| Filter Paper Type | ERT FF3 | Ahlstrom (Mt. Holly Springs, PA) #632 |
| Number of Pieces of Filter Paper | 5 | 7 |
| Confining Pressure | 4000g/(10cm)$^2$(~3.9 kPa) | 0.77 psi (5.2 kPa) |
| Test Fluid | Synthetic Urine | Sheep's Blood |
| Fluid Loading | 3.3 times wt of filter paper | 7.5 ml |
| Exposure Time: | | |
| Distribution | 3 Minutes Under Load | 15 Minutes |
| Rewet | 2 Minutes | 15 Seconds |

Signed and Sealed this

Fourteenth Day of January, 2003

JAMES E. ROGAN
*Director of the United States Patent and Trademark Office*